(12) United States Patent
Feinberg et al.

(10) Patent No.: US 11,213,518 B2
(45) Date of Patent: Jan. 4, 2022

(54) LIGANDS OF THE MU, KAPPA, AND DELTA OPIOID RECEPTORS

(71) Applicants: The Board of Trustees of the Leland Stanford Junior University, Stanford, CA (US); Memorial Sloan-Kettering Cancer Center, New York, NY (US)

(72) Inventors: Evan N. Feinberg, Fairfield, CA (US); Vijay S. Pande, Menlo Park, CA (US); Susruta Majumdar, St. Louis, MO (US); Gavril Pasternak, New York, NY (US)

(73) Assignees: The Board of Trustees of the Leland Stanford Junior University, Stanford, CA (US); Memorial Sloan-Kettering Cancer Center, New York, NY (US)

( * ) Notice: Subject to any disclaimer, the term of this patent is extended or adjusted under 35 U.S.C. 154(b) by 17 days.

(21) Appl. No.: 16/763,522

(22) PCT Filed: Nov. 14, 2018

(86) PCT No.: PCT/US2018/061129
§ 371 (c)(1),
(2) Date: May 12, 2020

(87) PCT Pub. No.: WO2019/099573
PCT Pub. Date: May 23, 2019

(65) Prior Publication Data
US 2020/0345715 A1 Nov. 5, 2020

Related U.S. Application Data

(60) Provisional application No. 62/585,796, filed on Nov. 14, 2017.

(51) Int. Cl.
*A61K 31/4453* (2006.01)
*A61K 31/415* (2006.01)
*A61K 9/00* (2006.01)

(52) U.S. Cl.
CPC ........ *A61K 31/4453* (2013.01); *A61K 31/415* (2013.01); *A61K 9/0019* (2013.01); *A61K 9/0053* (2013.01)

(58) Field of Classification Search
CPC .................................................. A61K 31/4453
See application file for complete search history.

(56) References Cited

U.S. PATENT DOCUMENTS 6,583,159 B1 * 6/2003 Patoiseau ............. C07D 211/58
514/317

OTHER PUBLICATIONS

PCT/US2018/061129 International Search Report, 2018.
PUBCHEM database record for 1-[5-(2-methylphenoxy)pentyl]piperidine https://pubchem.ncbi.nlm.nih.gov/substance/315896486; Aug. 2, 2016.
PUBCHEM database record for SID 3334708 https://pubchem.ncbi.nlm.nih.gov/substance/3334708; Jul. 28, 2005.
Andresen et al., (2016) "Auxotrophy-based High Throughput Screening assay for the identification of Bacillus subtilis stringent response inhibitors", Scientific Reports, 6:35824.
Nabuurs et al., (2007) "A flexible approach to induced fit docking.", J. Med. Chem., 50:6507-6518.
Manglik et al., (2016) "Structure-based discovery of opioid analgesics with reduced side effects." Nature, 537(7619):185-190.
Okude et al., (2015) "Identification of a Conformational Equilibrium That Determines the Efficacy and Functional Selectivity of the μ-Opioid Receptor.", Angew Chem Int Ed Engl., 54(52):15771-6.
Majumdar et al., (2011) "Truncated G protein-coupled mu opioid receptor MOR-1 splice variants are targets for highly potent opioid analgesics lacking side effects", Proc Natl Acad Sci USA, 108(49):19778-83.
Varadi et al.. (2016) "Mitragynine/Corynantheidine Pseudoindoxyls as Opioid Analgesics with Mu Agonism and Delta Antagonism, Which Do Not Recruit β-Arrestin-2.", J. Med. Chem., 59(18):8381-97.
Sounier et al., (2015) "Propagation of conformational changes during μ-opioid receptor activation.", Nature, 524:375-378.
Huang et al., (2015) "Structural insights into μ-opioid receptor activation.", Nature, 524:315-21.
Manglik et al., (2012) "Crystal structure of the μ-opioid receptor bound to a morphinan antagonist.", Nature, 485:321-326.
Feinberg et al., (2017) "Kinetic Machine Learning Unravels Ligand-Directed Conformational Change of μ Opioid Receptor.", BioRxiv, 170886.
Schwantes et al., (2013) "Improvements in Markov State Model Construction Reveal Many Non-Native Interactions in the Folding of NTL9.", J. Chem. Theory Comput., 9:2000-2009.
McGibbon et al., (2017) "Identification of simple reaction coordinates from complex dynamics.", J. Chem. Phys., 146:44109.
Offutt et al., (2016) "Enhancing Virtual Screening Performance of Protein Kinases with Molecular Dynamics Simulations.", J. Chem. Inf. Model., 56(10):1923-1935.
Swift et al., (2013) "Knowledge-Based Methods to Train and Optimize Virtual Screening Ensembles.", J. Chem. Theory Comput., 9(4):2000-2009.
Weiss et al., (2013) "Conformation guides molecular efficacy in docking screens of activated β-2 adrenergic G protein coupled receptor.", ACS Chem. Biol. 8:1018-1026.
Goldberg et al., (2010) "Stereochemical basis for a unified structure activity theory of aromatic and heterocyclic rings in selected opioids and opioid peptides." Perspect. Medicin. Chem., 4:1.
Sherman et al., (2006) "Use of an Induced Fit Receptor Structure in Virtual Screening", Chem. Biol. Drug Des., 67:83-84.

* cited by examiner

Primary Examiner — Rei Tsang Shiao
(74) Attorney, Agent, or Firm — Bozicevic, Field & Francis LLP; Jenny L. Buchbinder

(57) ABSTRACT

Ligands of the mu, kappa, and delta opioid receptors and methods of using them are disclosed. In particular, the invention relates to the discovery of new opioid receptor ligands based on molecular dynamics simulations of conformational states of the μ opioid receptor and the use of the identified opioid receptor ligands as analgesics, anti-diarrheal agents, and overdose reversal agents.

11 Claims, 20 Drawing Sheets

LIGANDS OF THE MU, KAPPA, AND DELTA OPIOID RECEPTORS

STATEMENT REGARDING FEDERALLY SPONSORED RESEARCH OR DEVELOPMENT

This invention was made with government support under contract GM08294 awarded by the National Institutes of Health. The government has certain rights in the invention.

TECHNICAL FIELD

The present invention pertains generally to ligands of opioid receptors, including the mu, kappa, and delta opioid receptors. In particular, the invention relates to the discovery of new opioid receptor ligands based on molecular dynamics simulations of conformational states of the μ opioid receptor and the use of the identified opioid receptor ligands as analgesics, anti-diarrheal agents, and overdose reversal agents.

BACKGROUND

A single class of proteins, the G-protein coupled receptors (GPCRs), comprises over one-third of the targets of all FDA-approved drugs[1]. One such GPCR, the μ opioid receptor (OR), epitomizes the benefits and drawbacks of existing GPCR drugs. Opioid chronic pain medications, such as morphine and hydrocodone, are μOR agonists that achieve their main therapeutic aim of analgesia, yet cause severe side effects, such as respiratory depression and addiction[2]. Like other GPCRs, μOR is not a binary switch. Rather, biophysical experiments indicate that GPCRs in general[3,4] and μOR in particular[5-9] traverse a spectrum of conformational states.

Computational chemists typically identify drug candidates by virtual screening of compounds against crystal structures of a protein despite the fact that some targets, like the μ opioid receptor and other members of the GPCR family, traverse many non-crystallographic states. There remains a need for better methods of modeling the multiplicity of functionally relevant pharmacologically predictive states to improve screening for opioid drugs with improved efficacy and reduced adverse effects.

SUMMARY

The invention relates to opioid receptor ligands and their various uses, including as analgesics, anti-diarrheal agents, and overdose reversal agents.

In certain embodiments, the invention includes an opioid receptor ligand that binds to one or more opioid receptors selected from the group consisting of a μ-opioid receptor (MOR), a δ-opioid receptor (DOR), and a κ-opioid receptor (KOR). In certain embodiments, the ligand is an opioid receptor agonist selected from the group consisting of 3,5-dimethyl-4-[6-(o-tolyloxy)hexyl]-1H-pyrazole (FMP4), 1-piperidino-5-(o-tolyloxy)pentane (FMP1), and 3,5-dimethyl-4-[6-(p-tolyloxy)hexyl]-1H-pyrazole (FMP16), and pharmaceutically acceptable salts thereof, and derivatives thereof.

In certain embodiments, the invention includes a composition comprising at least one opioid receptor ligand described herein and a pharmaceutically acceptable excipient. In another embodiment, the composition further comprises one or more other drugs for treating a disease or condition. For example, the composition may further comprise one or more analgesic agents, anti-inflammatory agents, anti-anxiety agents, or immunosuppressive agents.

In another embodiment, the invention includes a method of activating an opioid receptor, the method comprising contacting the opioid receptor with an effective amount of a composition comprising 3,5-dimethyl-4-[6-(o-tolyloxy)hexyl]-1H-pyrazole (FMP4), 1-piperidino-5-(o-tolyloxy)pentane (FMP1), or 3,5-dimethyl-4-[6-(p-tolyloxy)hexyl]-1H-pyrazole (FMP16), or a pharmaceutically acceptable salt thereof, or a combination thereof.

In another embodiment, the invention includes a method of treating pain in a subject, the method comprising administering a therapeutically effective amount of a composition comprising 3,5-dimethyl-4-[6-(o-tolyloxy)hexyl]-1H-pyrazole (FMP4), 1-piperidino-5-(o-tolyloxy)pentane (FMP1), 3,5-dimethyl-4-[6-(p-tolyloxy)hexyl]-1H-pyrazole (FMP16), or a pharmaceutically acceptable salt thereof, or a combination thereof. The pain can be, for example, postoperative pain, traumatic pain, neuropathic pain, or inflammatory pain.

In another embodiment, the invention includes a method of treating diarrhea in a subject, the method comprising administering a therapeutically effective amount of a composition comprising 3,5-dimethyl-4-[6-(o-tolyloxy)hexyl]-1H-pyrazole (FMP4), 1-piperidino-5-(o-tolyloxy)pentane (FMP1), 3,5-dimethyl-4-[6-(p-tolyloxy)hexyl]-1H-pyrazole (FMP16), or a pharmaceutically acceptable salt thereof, or a combination thereof.

An opioid receptor ligand (e.g., FMP1, FMP4, or FMP16) may be administered by any suitable mode of administration. In certain embodiments, the opioid receptor ligand is administered orally, intravenously, or subcutaneously to a subject. In another embodiment, the opioid receptor ligand is administered locally at a site of pain.

Multiple cycles of treatment may be administered to a subject. In certain embodiments, the opioid receptor ligand is administered according to a daily dosing regimen or intermittently.

In another embodiment, the invention includes a composition for use in the treatment of pain comprising 3,5-dimethyl-4-[6-(o-tolyloxy)hexyl]-1H-pyrazole (FMP4), 1-piperidino-5-(o-tolyloxy)pentane (FMP1), 3,5-dimethyl-4-[6-(p-tolyloxy)hexyl]-1H-pyrazole (FMP16), or a pharmaceutically acceptable salt thereof, or a combination thereof.

In another embodiment, the invention includes a composition for use in the treatment of diarrhea comprising 3,5-dimethyl-4-[6-(o-tolyloxy)hexyl]-1H-pyrazole (FMP4), 1-piperidino-5-(o-tolyloxy)pentane (FMP1), 3,5-dimethyl-4-[6-(p-tolyloxy)hexyl]-1H-pyrazole (FMP16), or a pharmaceutically acceptable salt thereof, or a combination thereof.

In another embodiment, the invention includes a composition for use in the treatment of a drug overdose comprising 3,5-dimethyl-4-[6-(o-tolyloxy)hexyl]-1H-pyrazole (FMP4), 1-piperidino-5-(o-tolyloxy)pentane (FMP1), 3,5-dimethyl-4-[6-(p-tolyloxy)hexyl]-1H-pyrazole (FMP16), or a pharmaceutically acceptable salt thereof, or a combination thereof.

These and other embodiments of the subject invention will readily occur to those of skill in the art in view of the disclosure herein.

DETAILED DESCRIPTION

Figure 1A:
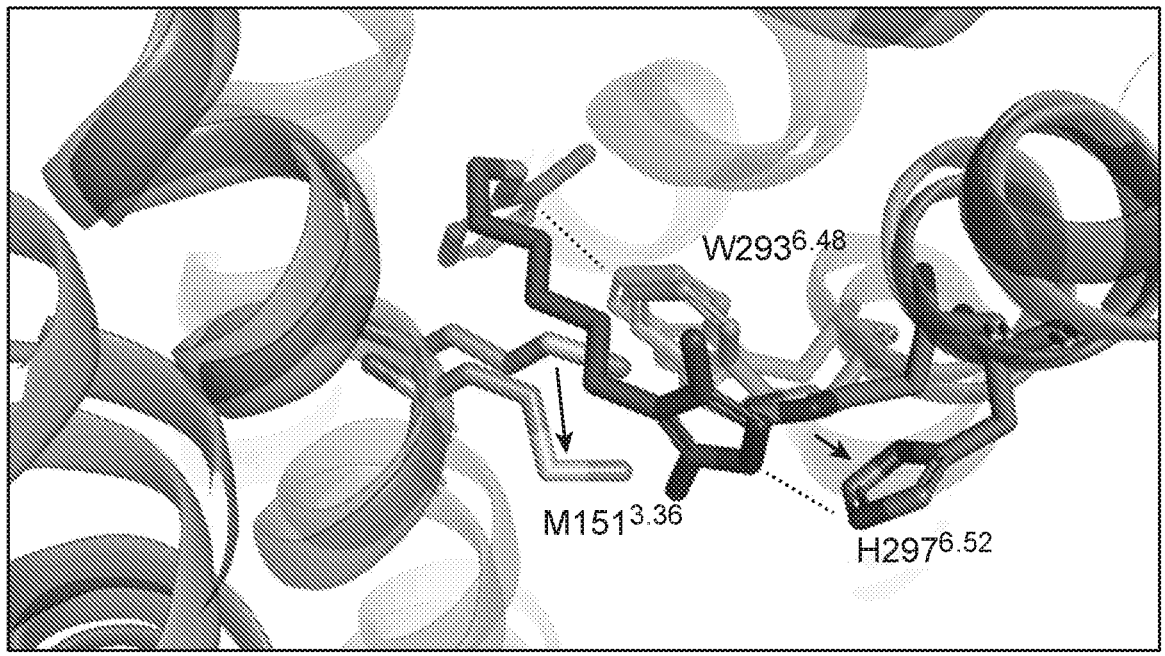
FIG. 1A shows active crystal structure (PDB: 5C1M) in light gray; MD State 3 in dark gray; docked pose of FMP4 to MD State 3 in dark gray. Solid arrows represent changes in MD from crystal structures. Dashed lines indicate non-covalent interactions between FMP4 and µOR binding pocket residues. Note that FMP4 would sterically clash with residues M151 and H297 in the active crystal, possibly accounting for its very low docking score to that structure. Movements of M151 and H297 enable favorable noncovalent ligand-protein interactions in a non-strained conformation of the ligand. Unlike the morphinan phenol, FMP4's phenyl ring engages with key activation residue W293 with a π-T aromatic interaction.

The practice of the present invention will employ, unless otherwise indicated, conventional methods of medicine, pharmacology, chemistry, and biochemistry within the skill of the art. Such techniques are explained fully in the literature. See, e.g., E. Freye and J. V. Levy *Opioids in Medicine: A Comprehensive Review on the Mode of Action and the Use of Analgesics in Different Clinical Pain States* (Springer, 2008); *Opioid Receptors: Methods and Protocols* (Methods in Molecular Biology, S. M. Spampinato, Humana Press, 2015); A. F. Casy and R. T. Parfitt *Opioid Analgesics: Chemistry and Receptors* (Springer, 1986); A. L. Lehninger, *Biochemistry* (Worth Publishers, Inc., current addition); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a ligand" includes a mixture of two or more ligands, and the like.

The term "about," particularly in reference to a given quantity, is meant to encompass deviations of plus or minus five percent.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

An "effective amount" of an opioid receptor ligand is an amount sufficient to effect beneficial or desired results, such as an amount that activates (i.e., agonist) or inhibits (i.e., antagonist) an opioid receptor. An effective amount can be administered in one or more administrations, applications, or dosages.

By "therapeutically effective dose or amount" of an opioid receptor ligand (e.g., FMP1, FMP4, or FMP16) is intended an amount that, when administered as described herein, brings about a positive therapeutic response with respect to treatment of an individual for pain, diarrhea, or a drug overdose. By "positive therapeutic response" is intended that the individual undergoing treatment exhibits an improvement in one or more symptoms, such as a reduction in pain or diarrhea or overdose reversal. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

As used herein, the terms "treatment," "treating," and the like, refer to obtaining a desired pharmacologic and/or physiologic effect (e.g., analgesia, antidiarrheal, or overdose reversal). The effect may be prophylactic in terms of completely or partially preventing a disease or symptom and/or may be therapeutic in terms of a partial or complete cure for a disease and/or adverse effects (e.g., pain) attributable to the disease.

"Substantially purified" generally refers to isolation of a substance (e.g., compound, molecule, agent) such that the substance comprises the majority percent of the sample in which it resides. Typically in a sample, a substantially purified component comprises 50%, preferably 80%-85%, more preferably 90-95% of the sample.

The terms "subject," "individual," and "patient," are used interchangeably herein and refer to any mammalian subject for whom diagnosis, prognosis, treatment, or therapy: is desired, particularly humans. Other subjects may include cattle, dogs, cats, guinea pigs, rabbits, rats, mice, horses, and so on. In some cases; the methods of the invention find use in experimental animals, in veterinary application, and in the development of animal models for disease, including, but not limited to, rodents including mice, rats, and hamsters; primates, and transgenic animals.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of new opioid receptor ligands based on molecular dynamics simulations of conformational states of the µ opioid receptor. In particular, the inventors have shown that FMP1, FMP4, and FMP16 are agonists of the mu, kappa, and delta opioid receptors (see Example 1). In order to further an understanding of the invention, a more detailed discussion is provided below regarding the identified opioid receptor ligands and their various uses, including as analgesics, anti-diarrheal agents, and overdose reversal agents.

A. Pharmaceutical Compositions

Opioid receptor ligands that can be used in the practice of the invention include various analogues and derivatives of 3,5-dimethyl-4-[6-(o-tolyloxy)hexyl]-1H-pyrazole (FMP4), 1-piperidino-5-(o-tolyloxy)pentane (FMP1), and 3,5-dimethyl-4-[6-(p-tolyloxy)hexyl]-1H-pyrazole (FMP16). In particular, such opioid receptor ligands have the ability to bind to one or more opioid receptors selected from the group consisting of a µ-opioid receptor (MOR), a δ-opioid receptor (DOR), and a κ-opioid receptor (KOR).

Such opioid receptor ligands (e.g., FMP1, FMP4, and FMP16) can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the opioid receptor ligand or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases, can be present as an excipient in the composition. Nonlimiting examples of, acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the opioid receptor ligand (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising one or more opioid receptor ligands described herein are in unit dosage form, meaning an amount of a conjugate or composition of the invention appropriate for a single dose, in a premeasured or pre-packaged form.

The compositions herein may optionally include one or more additional agents such as, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; and immune selective anti-inflammatory derivatives (ImSAIDs); anti-anxiety agents, such as barbiturates, including allobarbital, amobarbital, aprobarbital, alphenal, barbital, brallobarbital, pentobarbital, phenobarbital, and secobarbital; benzodiazepines, including Alprazolam (Xanax), Bromazepam (Lectopam, Lexotan), Chlordiazepoxide (Librium), Clonazepam (Klonopin, Rivotril), Clorazepate (Tranxene), Diazepam (Valium), Flurazepam (Dalmane), Lorazepam (Ativan), Oxazepam (Serax, Serapax), Temazepam (Restoril), Triazolam (Halcion); carbamates, including meprobamate (Miltown, Equanil), tybamate and lorbamate; antidepressants, including selective serotonin reuptake inhibitors (e.g., citalopram, fluvoxamine, escitalopram, paroxetine, sertraline, and fluoxetine), serotonin-norepinephrine reuptake inhibitors (e.g., venlafaxine and duloxetine), tricyclic antidepressants (e.g., imipramine, amitriptyline, nortriptyline and desipramine), tetracyclic antidepressants (e.g., Mirtazapine), and monoamine oxidase inhibitors (e.g.: phenelzine, isocarboxazid, tranylcypromine, moclobemide); immunosuppressive agents, such as steroidal agents (e.g., prednisone) or non-steroidal agents (e.g., sirolimus (Rapamune, Wyeth-Ayerst Canada), tacrolimus (Prograf, Fujisawa Canada), anti-IL2R daclizumab (Zenapax, Roche Canada), 15-deoxyspergualin, cyclosporin, methotrexate, rapamycin, Rapamune (sirolimus/rapamycin), FK506, and Lisofylline (LSF); and or other medications used to treat a subject for a condition or disease. Alternatively, such agents can be contained in a separate composition from the composition comprising an opioid receptor ligand (e.g., FMP1, FMP4, or FMP16) and co-administered concurrently, before, or after the composition comprising an opioid receptor ligand.

B. Administration

At least one therapeutically effective cycle of treatment with an opioid receptor ligand (e.g., FMP1, FMP4, or FMP16) will be administered to a subject for treatment of pain, diarrhea, or a drug overdose. By "therapeutically effective dose or amount" of an opioid receptor ligand (e.g., FMP1, FMP4, or FMP16) is intended an amount that, when administered as described herein, brings about a positive therapeutic response with respect to treatment of an individual for pain, diarrhea, or a drug overdose. By "positive therapeutic response" is intended that the individual undergoing treatment exhibits an improvement in one or more symptoms, such as a reduction in pain or diarrhea or overdose reversal.

In certain embodiments, multiple therapeutically effective doses of compositions comprising one or more opioid receptor ligands (e.g., FMP1, FMP4, or FMP16), and/or one or more other therapeutic agents, such as, but not limited to, anti-inflammatory/analgesic agents, including, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; and immune selective anti-inflammatory derivatives (ImSAIDs);

anti-anxiety agents, such as barbiturates, including allobarbital, amobarbital, aprobarbital, alphenal, barbital, brallobarbital, pentobarbital, phenobarbital, and secobarbital; benzodiazepines, including Alprazolam (Xanax), Bromazepam (Lectopam, Lexotan), Chlordiazepoxide (Librium), Clonazepam (Klonopin, Rivotril), Clorazepate (Tranxene), Diazepam (Valium), Flurazepam (Dalmane), Lorazepam (Ativan), Oxazepam (Serax, Serapax), Temazepam (Restoril), Triazolam (Halcion); carbamates, including meprobamate (Miltown, Equanil), tybamate and lorbamate; antidepressants, including selective serotonin reuptake inhibitors (e.g., citalopram, fluvoxamine, escitalopram, paroxetine, sertraline, and fluoxetine), serotonin-norepinephrine reuptake inhibitors (e.g., venlafaxine and duloxetine), tricyclic antidepressants (e.g., imipramine, amitriptyline, nortriptyline and desipramine), tetracyclic antidepressants (e.g., Mirtazapine), and monoamine oxidase inhibitors (e.g.: phenelzine, isocarboxazid, tranylcypromine, moclobemide); immunosuppressive agents, such as steroidal agents (e.g., prednisone) or non-steroidal agents (e.g., sirolimus (Rapamune, Wyeth-Ayerst Canada), tacrolimus (Prograf, Fujisawa Canada), anti-IL2R daclizumab (Zenapax, Roche Canada), 15-deoxyspergualin, cyclosporin, methotrexate, rapamycin, Rapamune (sirolimus/rapamycin), FK506, and Lisofylline (LSF); or other medications will be administered. Compositions may be administered in accordance with any medically acceptable method known in the art. The compositions are typically, although not necessarily, administered orally, via injection (subcutaneously, intravenously, or intramuscularly), by infusion, or locally. Additional modes of administration are also contemplated, such as intralesion, intraparenchymatous, pulmonary, rectal, transdermal, transmucosal, intrathecal, pericardial, intra-arterial, intraocular, intraperitoneal, and so forth.

The preparations according to the invention are also suitable for local treatment. In a particular embodiment, a composition of the invention is used for localized delivery of an opioid receptor ligand. For example, compositions may be administered locally at a site of injury causing pain. The particular preparation and appropriate method of administration can be chosen to target an opioid receptor ligand to µ-opioid receptors, δ-opioid receptors, or κ-opioid receptors in the nervous system or digestive tract.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising one or more opioid receptor ligands and other agents may be administered using the same or different routes of administration in accordance with any medically acceptable method known in the art.

In another embodiment of the invention, the pharmaceutical compositions comprising one or more opioid receptor ligands and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising an opioid receptor ligand as provided herein to a patient suffering from a condition that is responsive to treatment with an opioid receptor ligand contained in the conjugate or composition. The method comprises administering, via any of the herein described modes, a therapeutically effective amount of the conjugate or drug delivery system, preferably provided as part of a pharmaceutical composition. The method of administering may be used to treat any condition that is responsive to treatment with an opioid receptor ligand. More specifically, the compositions herein are effective in treating inflammatory disorders.

Those of ordinary skill in the art will appreciate which conditions a specific opioid receptor ligand can effectively treat. The actual dose to be administered will vary depending upon the age, weight, and general condition of the subject as well as the severity of the condition being treated, the judgment of the health care professional; and conjugate being administered. Therapeutically effective amounts can be determined by those skilled in the art, and will be adjusted to the particular requirements of each particular case.

A purified opioid receptor ligand (again, preferably provided as part of a pharmaceutical preparation) can be administered alone or in combination with one or more other therapeutic agents, such as other drugs for treating an inflammatory disorder, a neurodegenerative disease, a neuroimmune disease, an autoimmune disease, cancer, an infection, or systemic inflammation, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. In certain embodiments, multiple therapeutically effective doses of an opioid receptor ligand and/or other therapeutic agents will be administered according to a daily dosing regimen or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, opioid receptor ligands will be administered twice-weekly or thrice-weekly for an extended period of time, such as for 1, 2, 3, 4; 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. Preferred compositions are those requiring dosing no more than once a day.

An opioid receptor ligand can be administered prior to, concurrent with, or subsequent to other agents. If provided at the same time as other agents, opioid receptor ligands can be provided in the same or in a different composition. Thus, one or more opioid receptor ligands and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising an opioid receptor ligand and a dose of a pharmaceutical composition comprising at least one other agent, such as another opioid receptor ligand or drug for treating an inflammatory disorder, which in combination comprise a therapeutically effective dose, according to a particular dosing regimen. Similarly, one or more opioid receptor ligands and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

C. Kits

The invention also provides kits comprising one or more containers holding compositions comprising at least one opioid receptor ligand (e.g., FMP1, FMP4, or FMP16, or pharmaceutically acceptable salts or derivatives thereof) and optionally one or more other agents, such as analgesic agents, anti-inflammatory agents, anti-anxiety agents, or immunosuppressive agents. Compositions can be in liquid form or can be lyophilized. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for methods of, using the compositions comprising the opioid receptor ligands for treating a subject, for example, for pain, diarrhea, or a drug overdose. The package insert can be an unapproved draft package insert or can be a package insert approved by the Food and Drug Administration (FDA) or other regulatory body.

D. Machine Learning Methodology

While the identification of molecules FMP1, FMP4, FMP16, and derivatives or analogues thereof could in theory be realized through a variety of experimental or computational means, it is noteworthy that the use of FMP1, FMP4, and FMP16 as binders to and modulators of the delta, and kappa opioid receptors was identified in this case using novel means. In particular, molecular dynamics simulation, molecular docking, and machine learning were deployed in series in a way that previously did not exist to identify small molecule ligands of the μ receptor. Molecular dynamics simulations can serve as one of several mechanisms (e.g., monte carlo based simulations and normal mode analysis) to generate physically plausible conformational states of proteins. In turn, molecular docking can serve as one of several mechanisms (e.g., further molecular dynamics simulation, monte carlo based simulation) to hypothesize the binding energy of a given ligand to that conformational state. Finally, any one of several machine learning algorithms (e.g., random forests, support vector machines, linear regression, neural networks) can provide a mapping of estimated affinities of a given ligand to multiple conformational states of a protein to that ligand's overall binding affinity or other metrics of activity (e.g., agonism or inhibition).

In this case, we deployed molecular dynamics simulation to generate conformers of the μ Opioid Receptor using its crystal structure as a starting point. Subsequently, we used unsupervised machine learning (in this case, time-structure based independent component analysis) to choose a tractable subset of conformations to which to perform molecular docking. We then docked a library of ligands with known binding free energies to each conformational state. This produced a matrix of size N×K where N is the number of ligands and K is the number of states and the (i, j) entry in the matrix is the docking score of Ligand i to Conformation j. Penultimately, a Random Forest was trained to map the per-state docking scores of a given ligand to a given binding and agonism of that molecule. Finally, a library of ligands with unknown activity toward μ Opioid Receptor was computationally screened by docking each ligand to each μ Opioid Receptor conformational state, obtaining the associated docking scores, and using the pre-trained Random Forest to predict each ligand's binding affinity and agonism. The ligands determined to have the highest ability to bind to and to be an agonist for the μ Opioid Receptor were then experimentally tested for activity at μ Opioid Receptor in the laboratory. The most promising series reflecting experimental activity consisted of molecules FMP1, FMP4, and FMP16.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Machine Learning Harnesses Molecular Dynamics to Discover New μ Opioid Chemotypes Our central thesis is that μOR samples a multiplicity of functionally relevant and pharmacologically predictive states. We have tested this hypothesis by developing novel computational methods to identify and incorporate these states, both yielding an Increased AUC in opiate activity prediction and empowering, the discovery of new opioid scaffolds.

Specifically, we posit that identifying important μOR states beyond the two crystal structures[10,11] would improve the ability to predict the activity of ligands at the receptor. To test this hypothesis, we conducted long timescale MD simulations of μOR either unliganded or bound to one of several agonists: BU72[12], Sufentanil[13], TRV130[14], and IBNtxA[7], providing a heterogeneous yet comprehensive spectrum of conformations that μOR can adopt. This dataset expands upon previous work,[15,16] which focused on the conformational dynamics of the receptor. To systematically process such a large parallel MD dataset, consisting of an unprecedented 1.1 milliseconds of μOR simulation, we applied a kinetically motivated machine learning approach that (1) identified the reaction coordinates of μOR using the cutting-edge Sparse tICA algorithm[17-19] and (2) defined discrete receptor states using Minibatch K-Means clustering[20].

This unsupervised step uncovered key conformations of μOR, consisting both of intermediates between as well as non-canonical states distinct from the crystal structures (FIG. 1, ref.[15]). In light of recent studies[21,22], these structures are potentially druggable states that can be directly employed to enrich rational drug discovery campaigns for μOR. To realize this potential, we trained supervised machine learning models that demonstrate significant improvement in two binary classifier tasks (Table 1): (1) the ability to distinguish agonists from antagonists, and (2) the ability to distinguish binders from non-binders at μOR.

Figure 5:
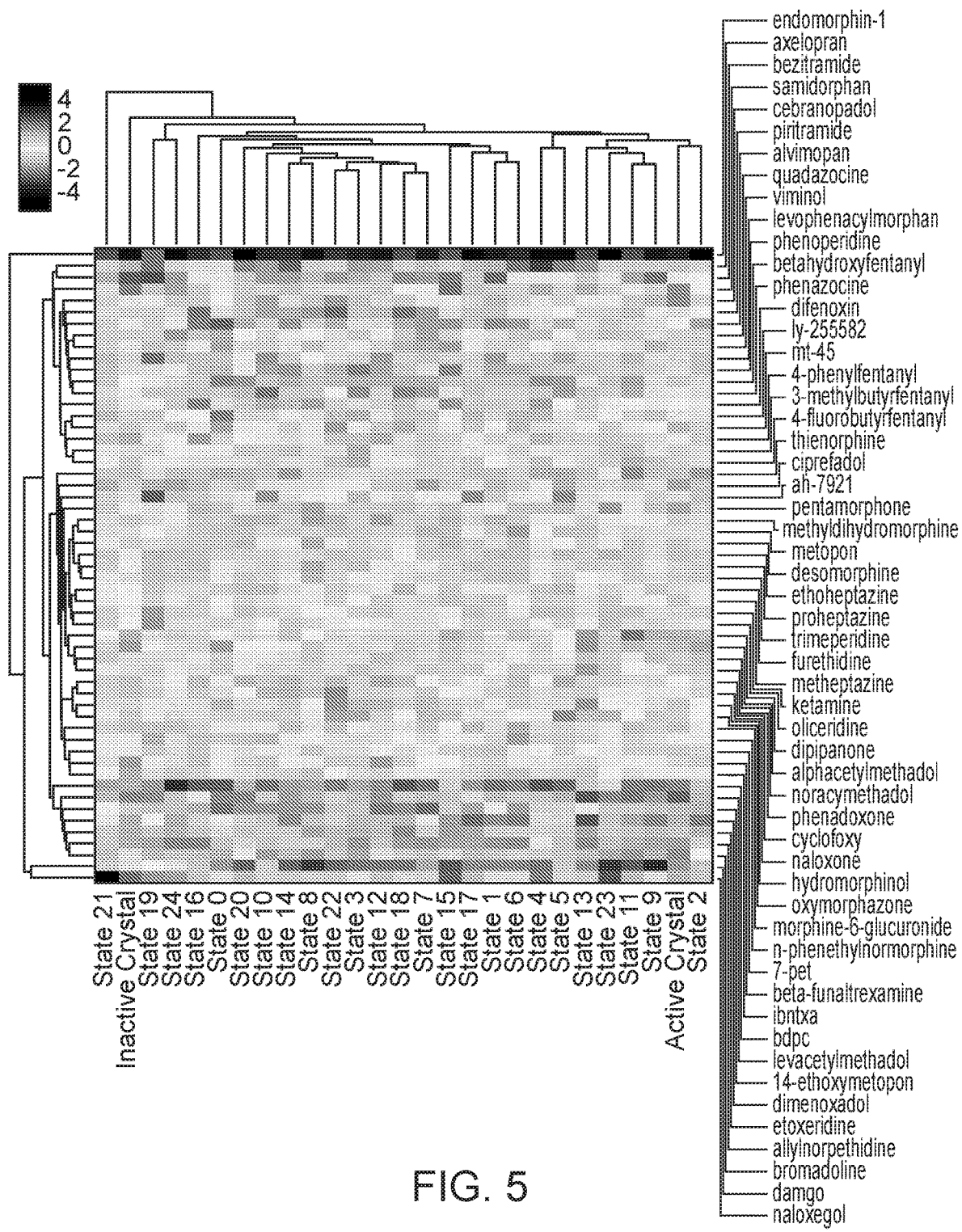
FIG. 5 shows visualization of a subset of the feature matrix (X matrix), the input to the machine learning algorithm. Each row is an opioid ligand, each column is a feature (docking scores to each of MD States 0-24 and to each crystal structure). Therefore, entry (i, j) in the matrix is the docking score of the i'th ligand to the j'th conformational state. For visualization, each row is normalized to mean zero and unit variance. Also for visualization, Rows (ligands) and columns (features) are also hierarchically clustered.

Specifically, random forest[23], one of the most typically employed machine learning tools in drug design, were deployed to connect structure to function. A database of opioids with known pharmacologies was docked to both the crystal structures as well as to a representative conformation of each state. The docking scores of each ligand to each MD conformation were then used as the input (FIG. 5), or feature matrix, to binary classifier[24] models for both agonism and binding at μOR.

This combination of structural information from both crystallography and MD yielded statistically significant enrichment in both tasks. Model performance is evaluated using the Receiver Operating Characteristic (ROC) Area Under the Curve (AUC[24]) and stratified cross-validation (Methods). Cross-validation is a pseudo-prospective validation of the model which estimates the experimental performance on previously unseen query ligands. The new method—which incorporates docking to the MD states in addition to the crystal structures—achieved a median AUC improvement of 0.11 in agonism and of 0.15 in binding compared to the crystal structures alone (Tables 1, 6, and 7).

In contrast to many previous virtual screening approaches, which are predicated solely on ligand-derived features, the machine-learning approach described here is based on the affinities of a given ligand toward each μOR conformation. As a further test of this method's robustness to agonism, scaffold splits were employed. Specifically, a series of models were trained in which analogs of either methadone or fentanyl were removed from the training data and placed in a held-out test set (Tables 1, 4, and 6). In other words, none of these models had any a priori knowledge of methadone (or, alternately, fentanyl) analogs. Nevertheless, the models successfully distinguished both methadone- and fentanyl-derived agonists from random sets of antagonists. Analogous scaffold splits were defined for the binding prediction task, yielding comparable gains in AUC (Tables 1 and 7). Therefore, since this method does not explicitly incorporate the chemical makeup of the ligand, it is in principle better equipped to discover new opioid-active scaffolds in addition to derivatives of existing ones.

In practice this method identified several novel opioid-active scaffolds that were verified experimentally. First, 133,564 small molecules from the Stanford Compound Library were docked to both crystal structures and the computationally modeled conformers of μOR. This step yielded a 133,564 row by 27 column feature matrix, where entry (i, j) is the docking score of the i'th ligand to the j'th conformational state. The two trained random forest models for binding and agonism were applied to each library ligand, yielding a final score computed from the product of the two values:

P(binder∩agonist|model)=P(binder|model$_b$)·P(agonist|model$_a$)

Both model performance and scaffolds of hits are highly sensitive to the pIC50 cutoff chosen for binary classifiers (Table 7). While models with a lower affinity threshold for binding generally have higher AUC, their top hits are more biased toward compounds with a tertiary, basic nitrogen similar to known scaffolds. Therefore, we used random forests models with a pIC50 cutoff of 8.0 (100 nM) to optimize for novel scaffold discovery.

Figure 6:
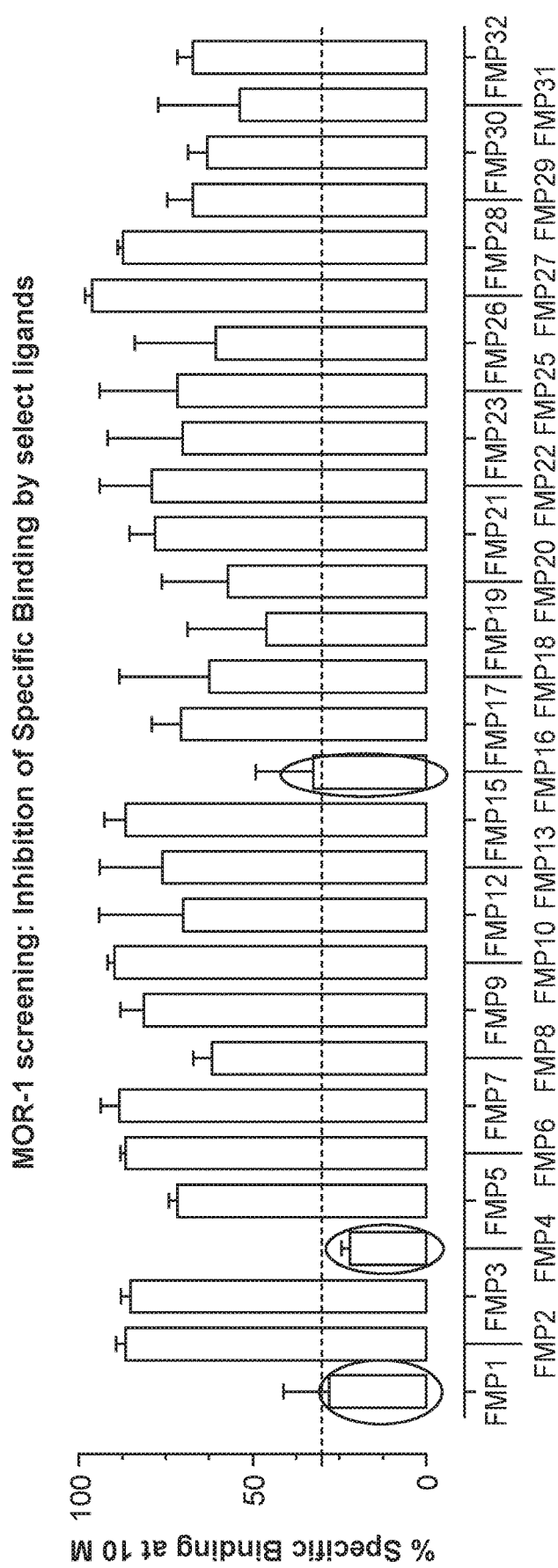
FIG. 6 shows screening of MOR-1 binders: Inhibition of $^{125}$IBNtxA specific binding at MOR-1 was carried out at a single dose 10 µM concentration. Three compounds FMP1, 4 and 16 (circled) showed ≥30% inhibition of MOR-1 binding (red dotted line represents compounds showing ≥30% inhibition). Each panel is a representative experiment that has been independently replicated at least three times.
Figure 7A:
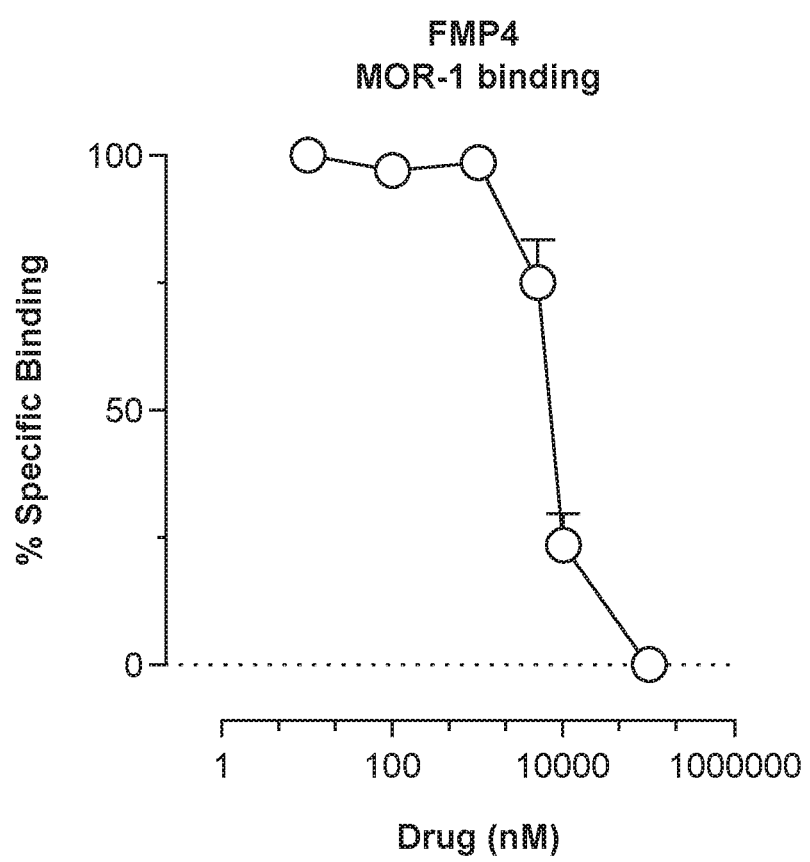
FIGS. 7A-7C show competition assays at MOR-1, KOR-1 and DOR-1 against FMP4. Competition studies were performed with FMP4 against $^{125}$I-IBNtxA (0.1 nM) in membranes from CHO cells stably expressing the indicated cloned mouse opioid receptors Each figure is a representative experiment that has been independently replicated at least three times. Error bars represent the SEM of triplicate samples. Error bars that cannot be seen are smaller than the size of the symbol. FMP4 had 3217±153 nM, 2503±523 nM and 8143±1398 nM affinity at MOR-1 (FIG. 7A), KOR-1 (FIG. 7B), and DOR-1 (FIG. 7C) respectively.
Figure 7B:
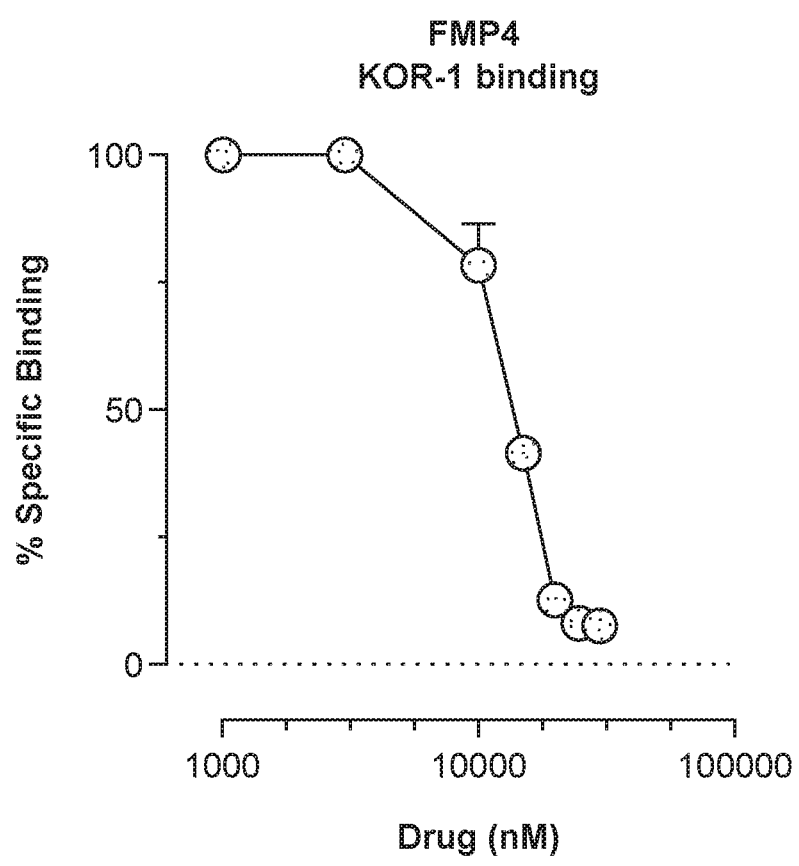
Figure 7C:
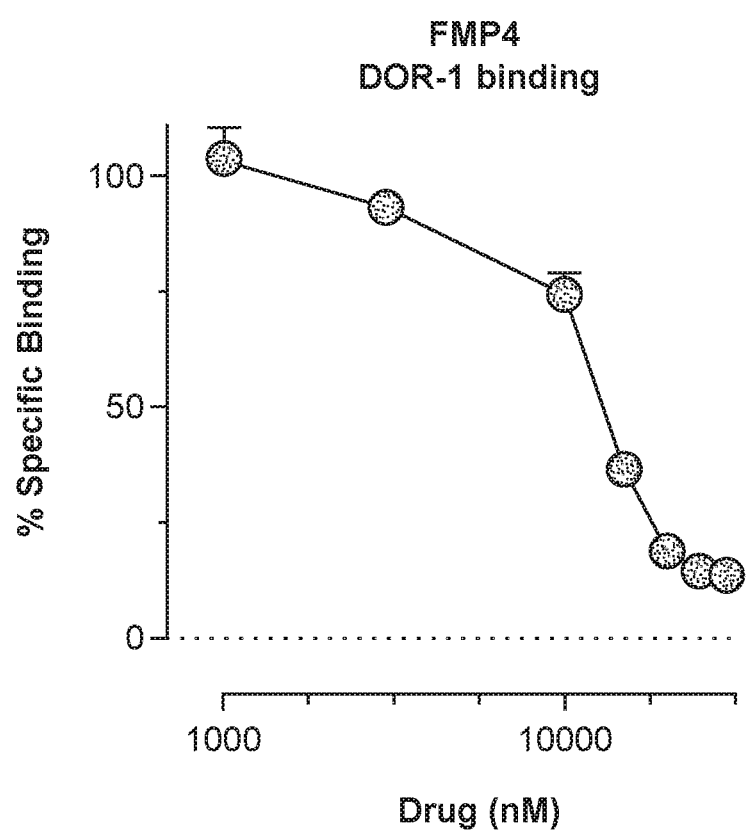
Figure 8:
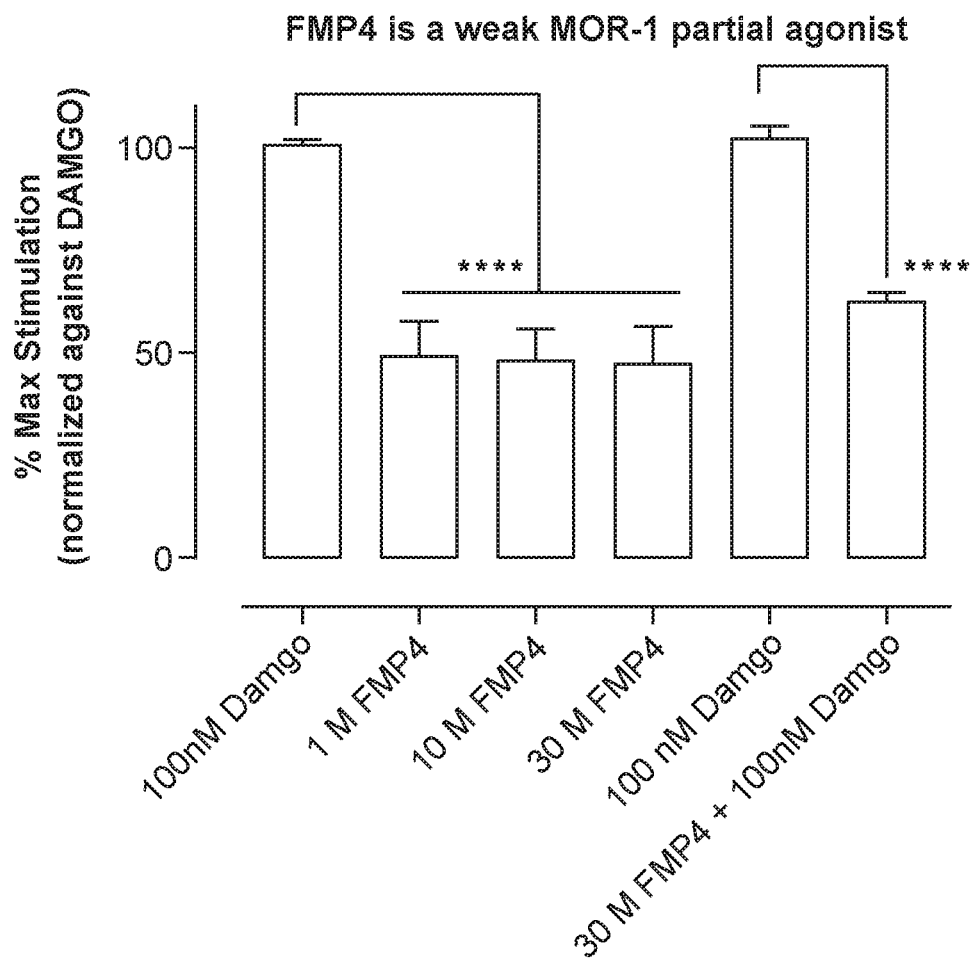
FIG. 8 shows that FMP4 is a partial agonist in [35S]-GTPγS assays in MOR-1 expressing CHO cells. Results are pooled from 3 independent replications and are expressed as mean±SEM. FMP4 stimulates GTPγS binding at doses 1, 10 and 30 µM respectively and shows a ceiling effect consistent with partial agonism at the receptor in comparison to the prototypic full MOR-1 agonist DAMGO at 100 nM (one-way ANOVA followed by Tukeys post hoc comparisons test, *significantly different from control (p<0.0001)). FMP4 at a dose of 30 µM also antagonized the GTPγS stimulation of 100 nM DAMGO consistent with its partial agonism at the receptor.
Figure 9:
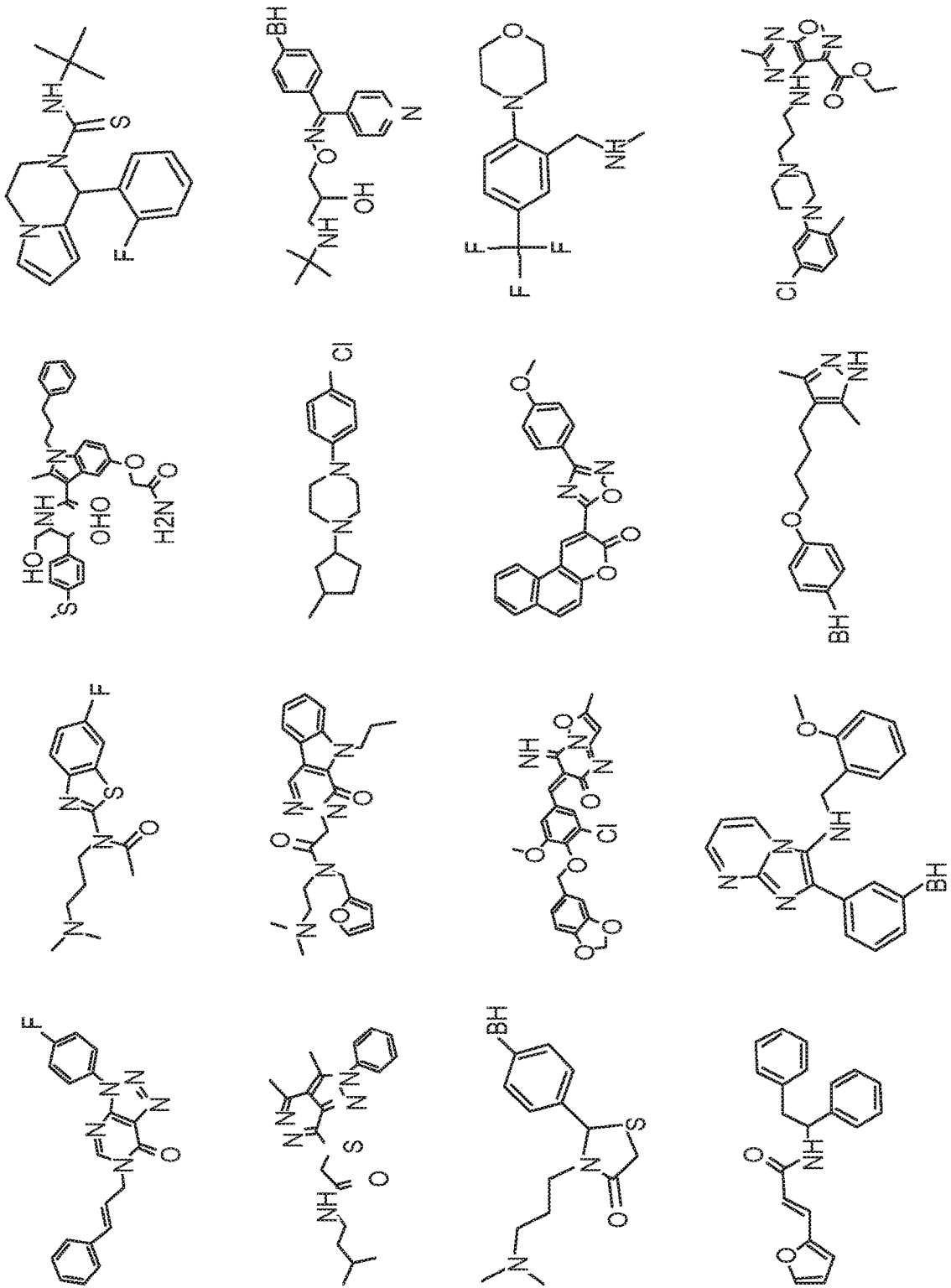
FIG. 9 shows the top hits for "All, pIC50 cutoff=8.0" affinity model, i.e. affinity model where training data is defined in the following way: µOR binders are those with measurable pIC50≥8.0 according to Chembl and are agonists/antagonists at µOR according to Wikipedia, whereas µOR non-binders are those with measurable pIC50<8.0 or listed as "Not Active" in Chembl are excluded.
Figure 9:
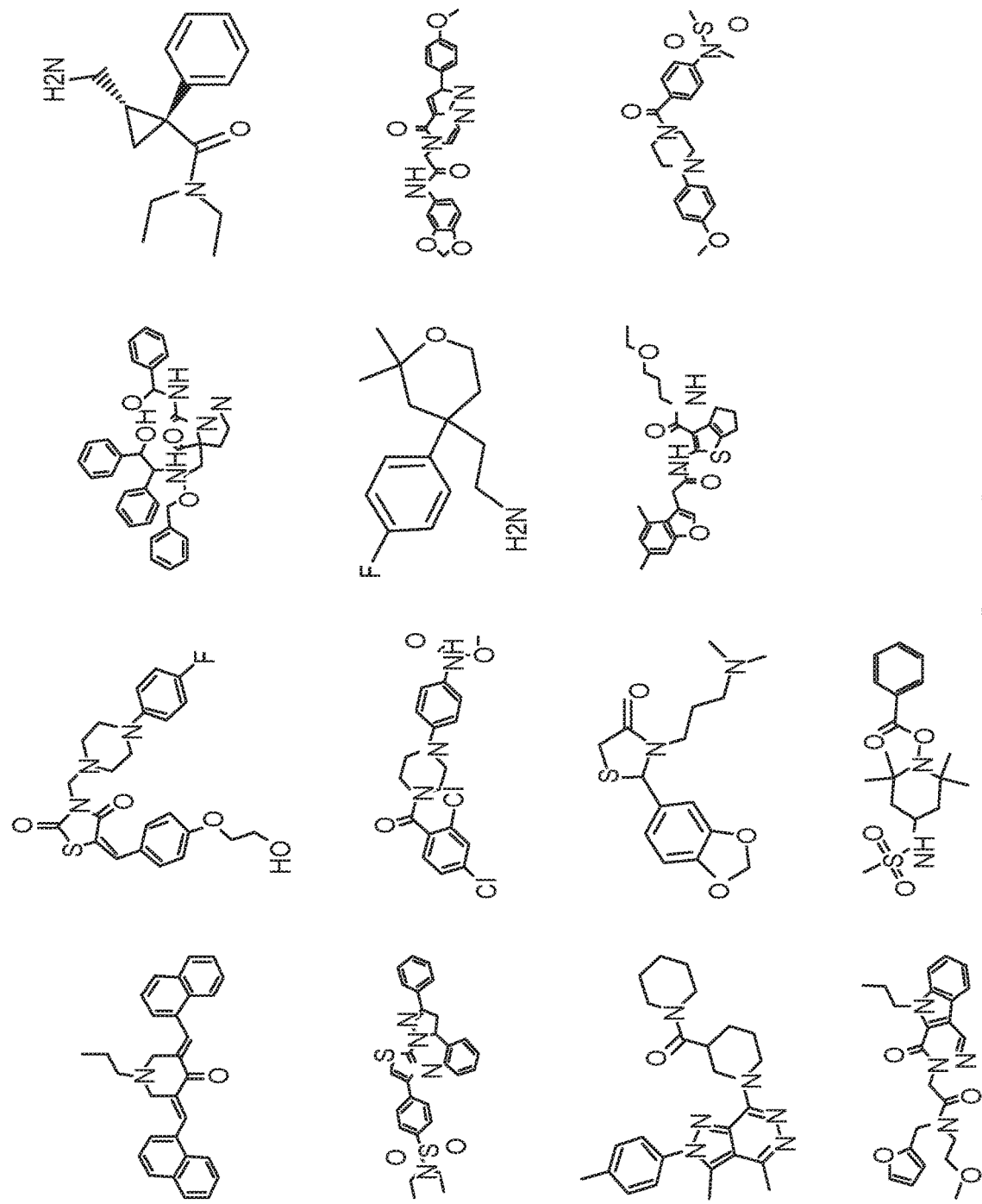
Figure 10:
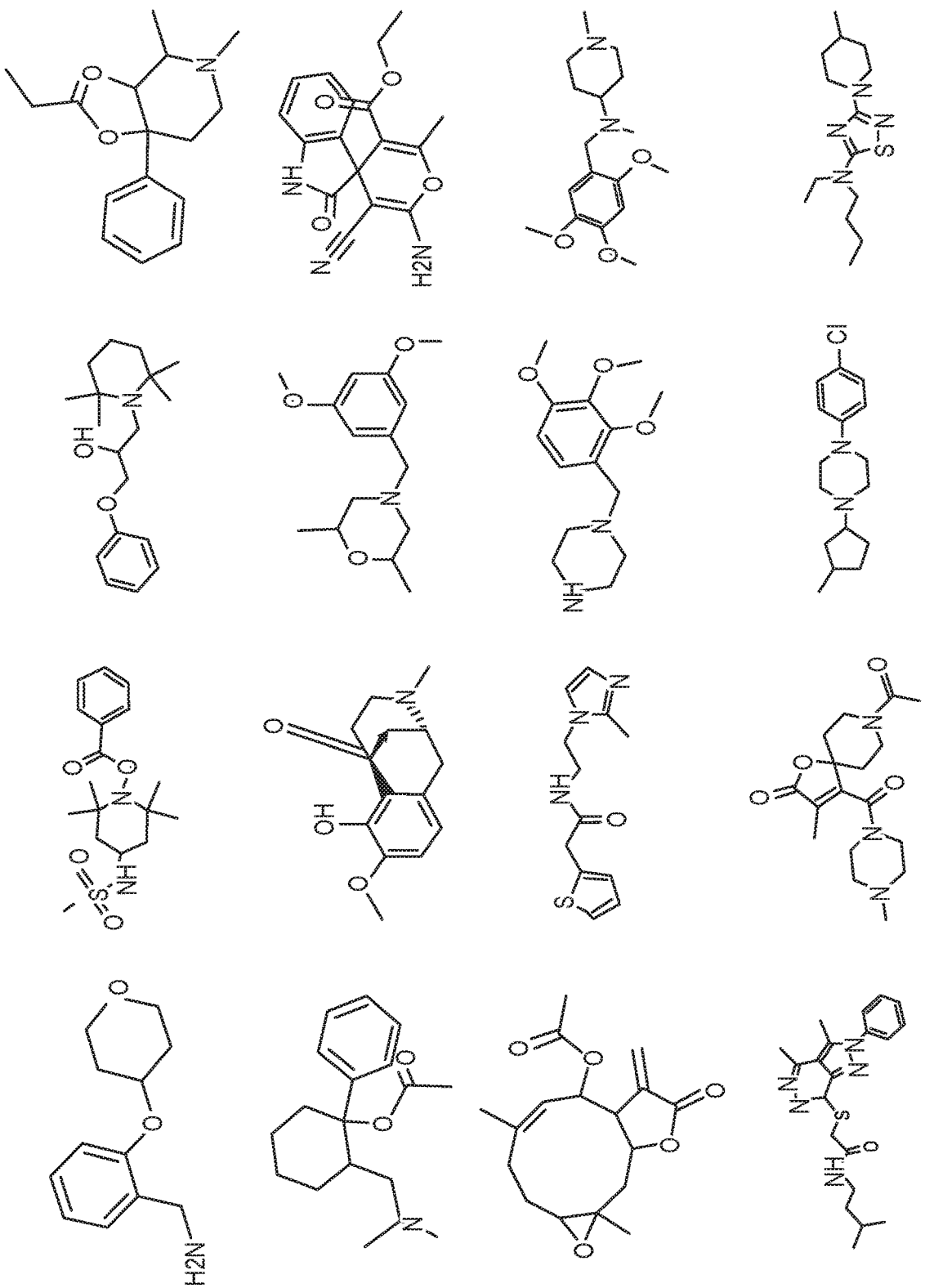
FIG. 10 shows Top hits for "Measured pIC50 cutoff=8.0" affinity model, i.e. affinity model where training data is defined in the following way: µOR binders are those with measurable pIC50≥8.0 according to Chembl and are agonists/antagonists at µOR according to Wikipedia, whereas µOR non-binders are those with measurable pIC50<8.0. Drugs listed as "Not Active" in Chembl are excluded.
Figure 10:
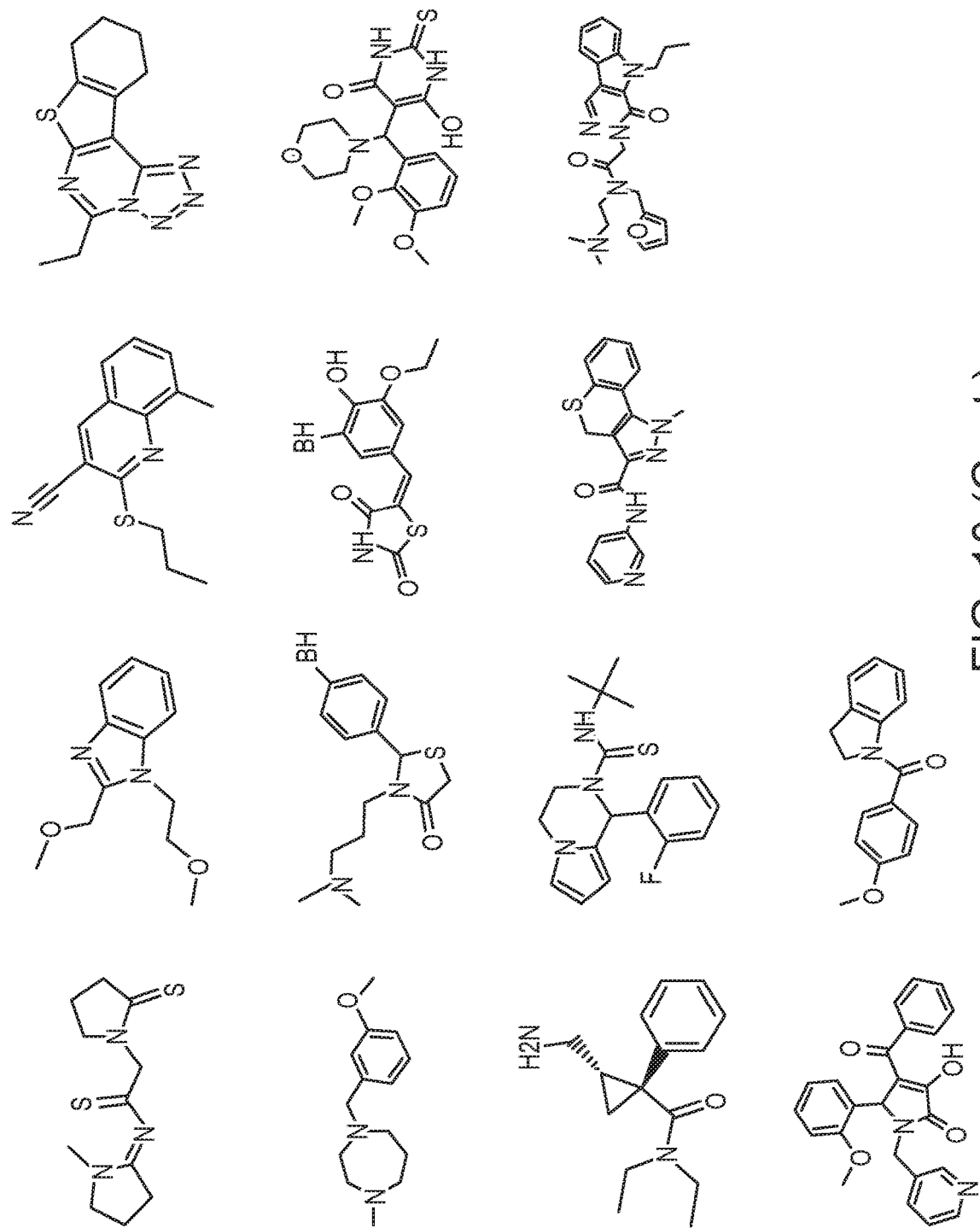

The thirty highest scoring, immediately purchasable compounds were then experimentally assayed. At least four of the thirty compounds exhibited micromolar affinity for μOR (FIG. 6, Table 9). FMP4, because of its unique structure—namely, no basic amine or phenol—was characterized further in binding assays in opioid transfected cell lines. FMP4 had 3217±153 nM, 2503±523 nM and 8143±1398 nM affinity at MOR-1, KOR-1 and DOR-1 respectively (FIGS. 7A-7C). FMP 4 was also a weak MOR-1 partial agonist in [$^{35}$S]GTP7S functional assays. (FIG. 8). Structurally similar FMP4-like compounds in the same data set were also characterized in binding assays and at least two compounds (FMP1 and FMP16) showed <10 μM affinity at MOR-1 (Table 9). Structure activity studies using classical medicinal chemistry approaches using these templates as a starting point may lead to compounds with higher affinities at the receptor.

Based on these results, opioid prediction is enriched by incorporating conformational states that are unforeseeable from crystallography alone and stabilized by ligands in simulation. Notably, FMP4 is distinct from known opioid agonists and antagonists, with a maximum Tanimoto score of 0.44 to the ligands listed in Table 2. Underscoring its difference is FMP4's lack of a basic tertiary amine and phenol, that are the hallmark of synthetic opioids, from classic to current experimental molecules[5,7,14,25].

Figure 1B:
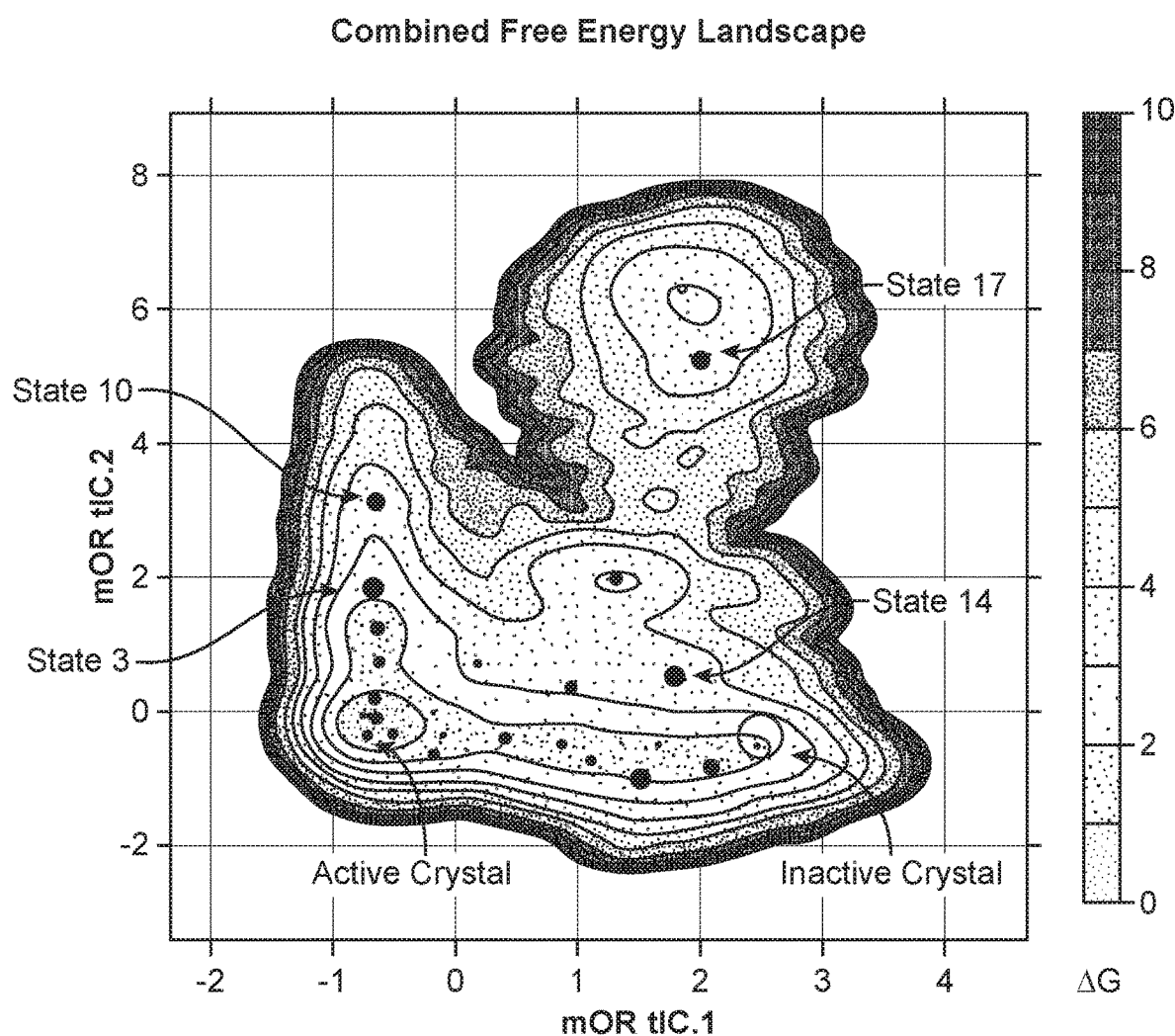
FIG. 1B shows the free energy landscape of µOR projected onto its two slowest collective degrees of freedom. Whereas tICA coordinate 1 separates the active and inactive (PDB: 4DKL) crystal structures, tICA coordinate 2 is an orthogonal degree of freedom defining several non-crystallographic inactive and active-like states. Such states include State 3, critical for FMP4's ability to engage with the receptor.
Figure 2:
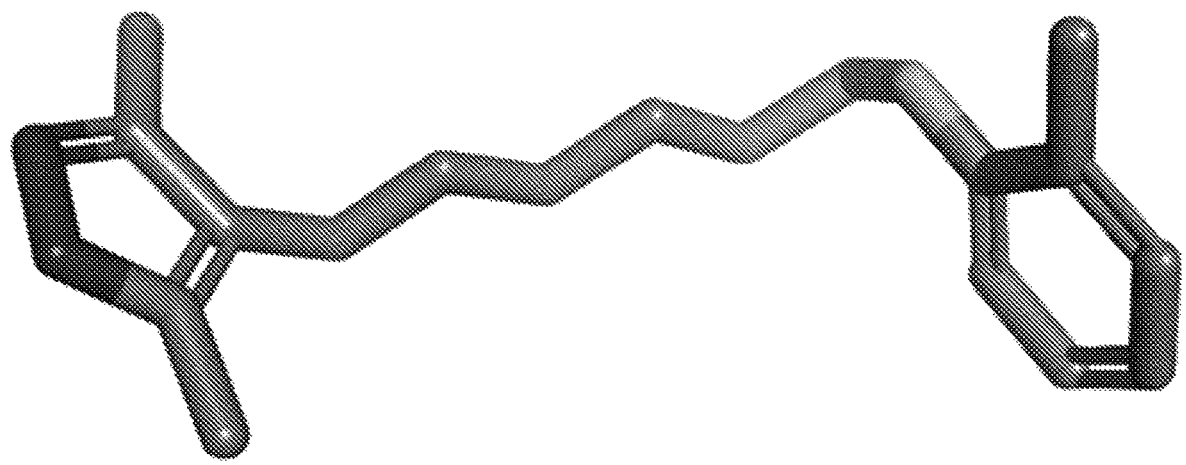
FIG. 2 shows the compound FMP4 (Pubchem ID: 2057658). FMP4 exhibits 3.2 µM affinity for µOR with weak partial agonism.
Figure 3A:
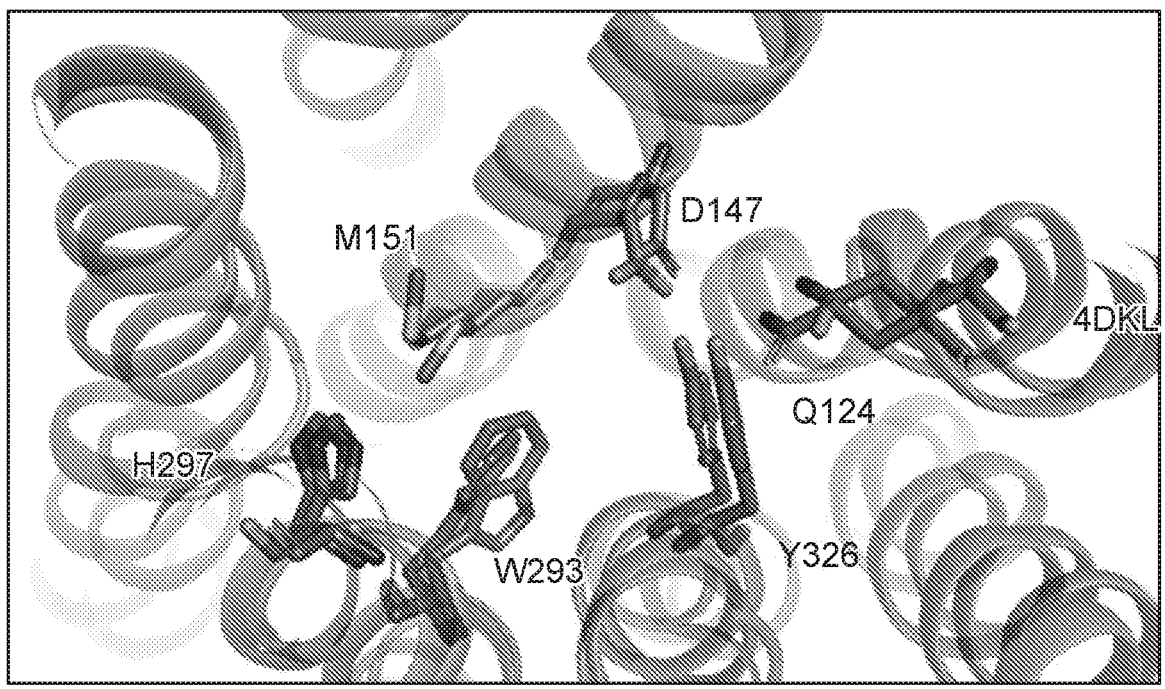
FIGS. 3A-3F show, binding pocket views of important conformational states of µOR derived from MD simulation by measurement of the largest mean reduction in Gini impurity for random forest models of binding and of agonism. The conformational states shown are state 1 (FIG. 3A), state 2 (FIG. 3B), state 3 (FIG. 3C), state 14 (FIG. 3D), state 17 (FIG. 3E), and state 18 (FIG. 3F).
Figure 3B:
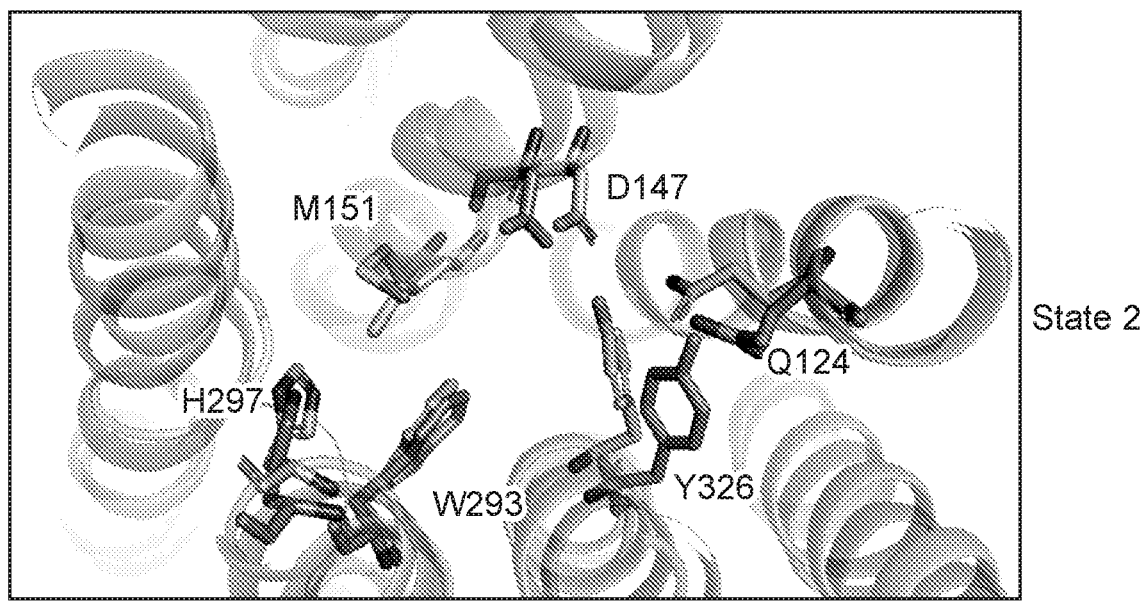
Figure 3C:
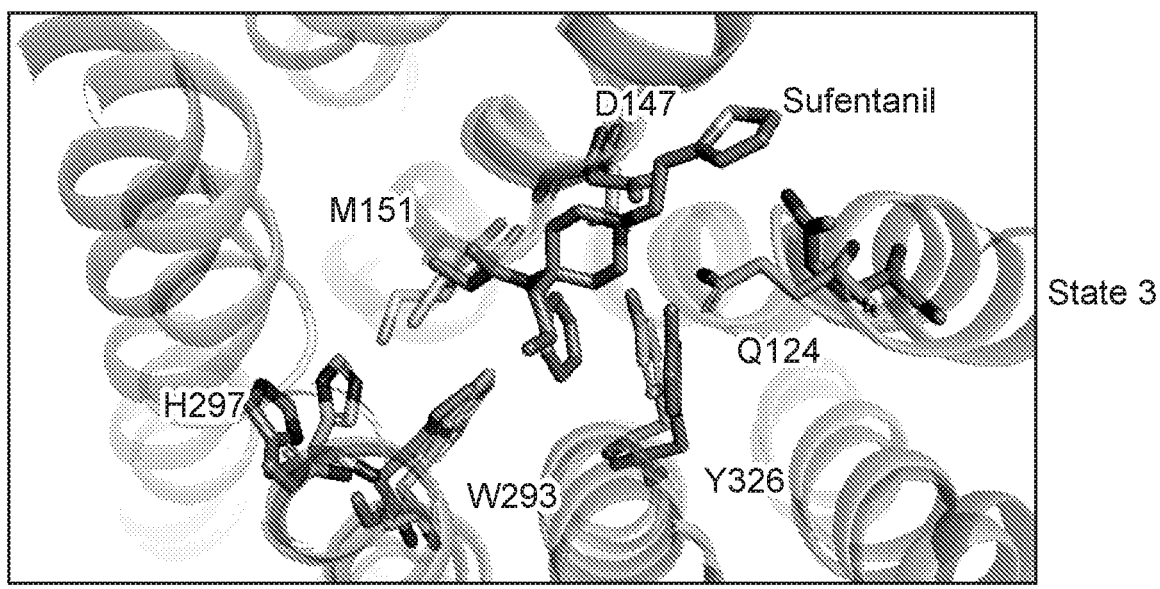
Figure 3D:
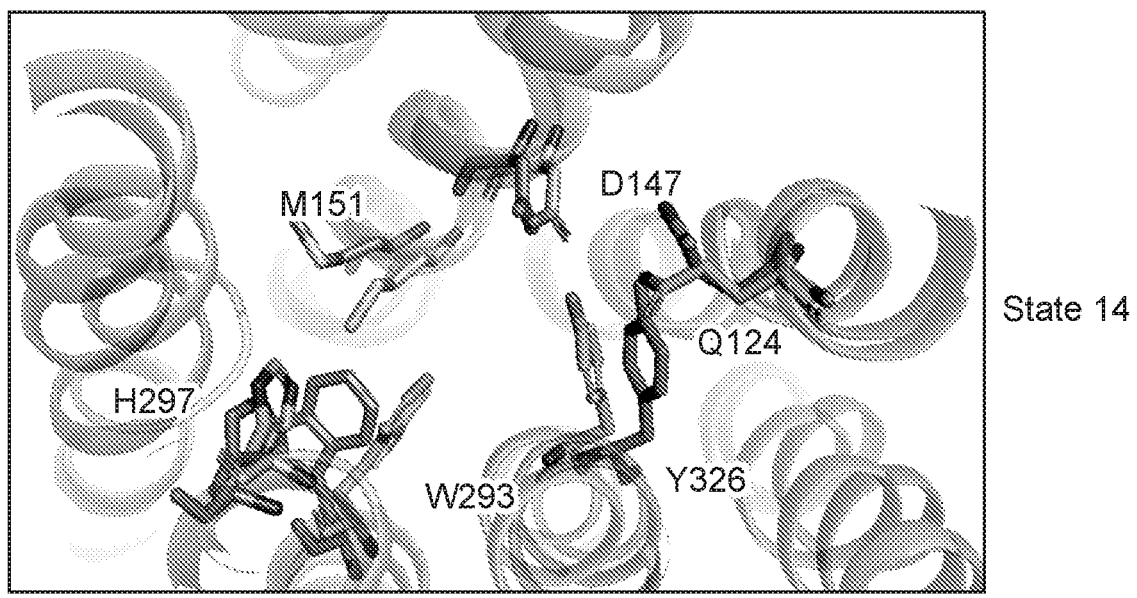
Figure 3E:
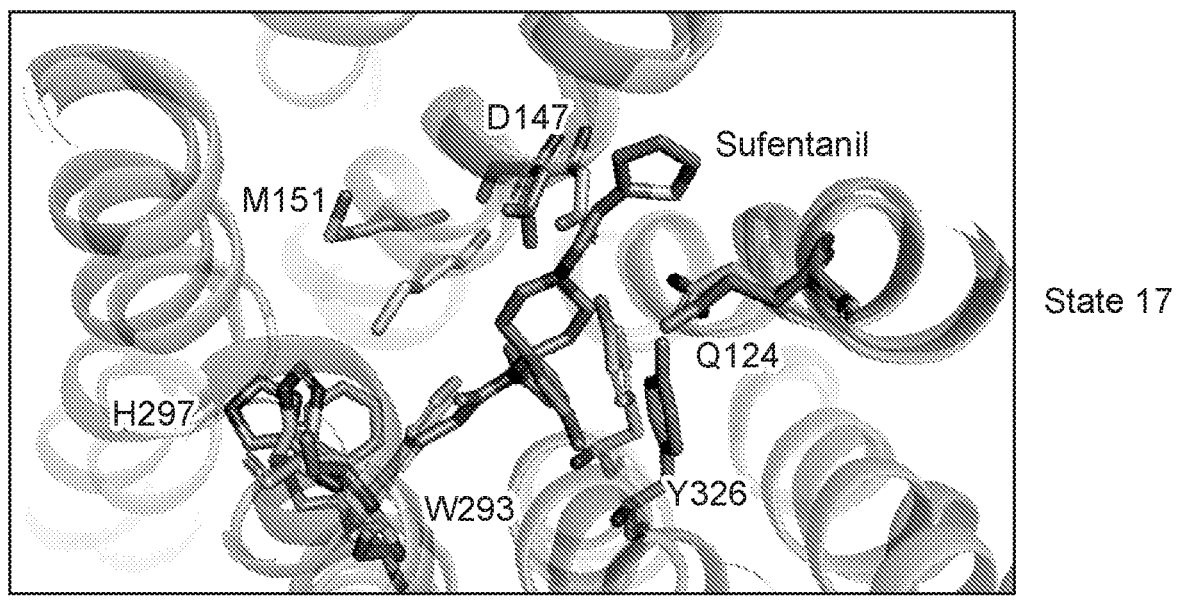
Figure 3F:
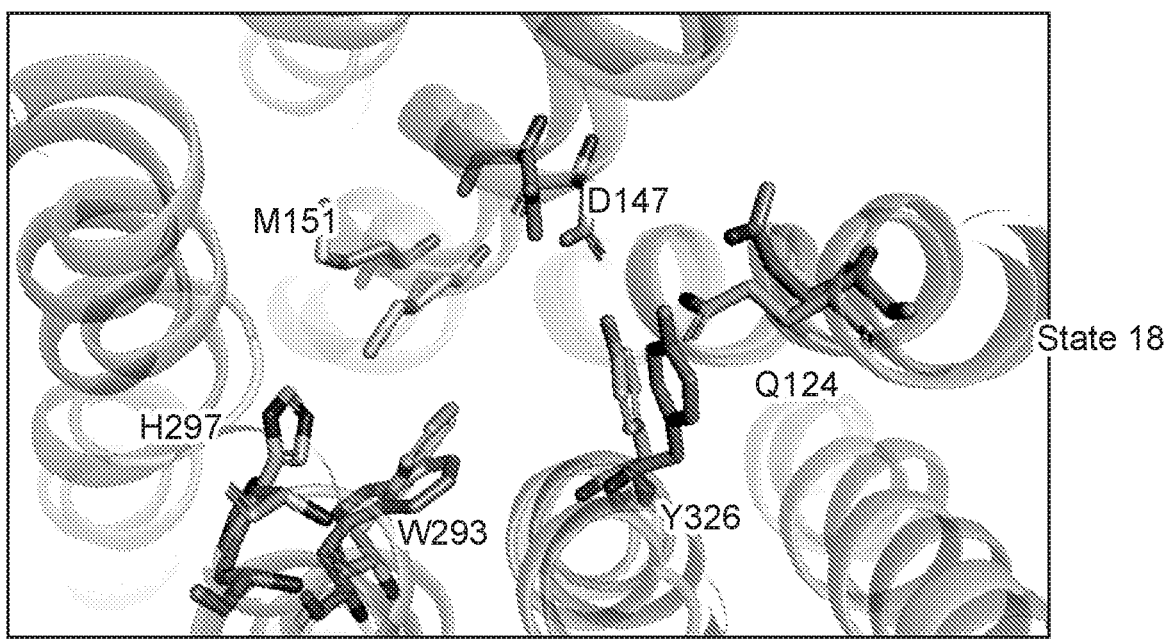
Figure 4:
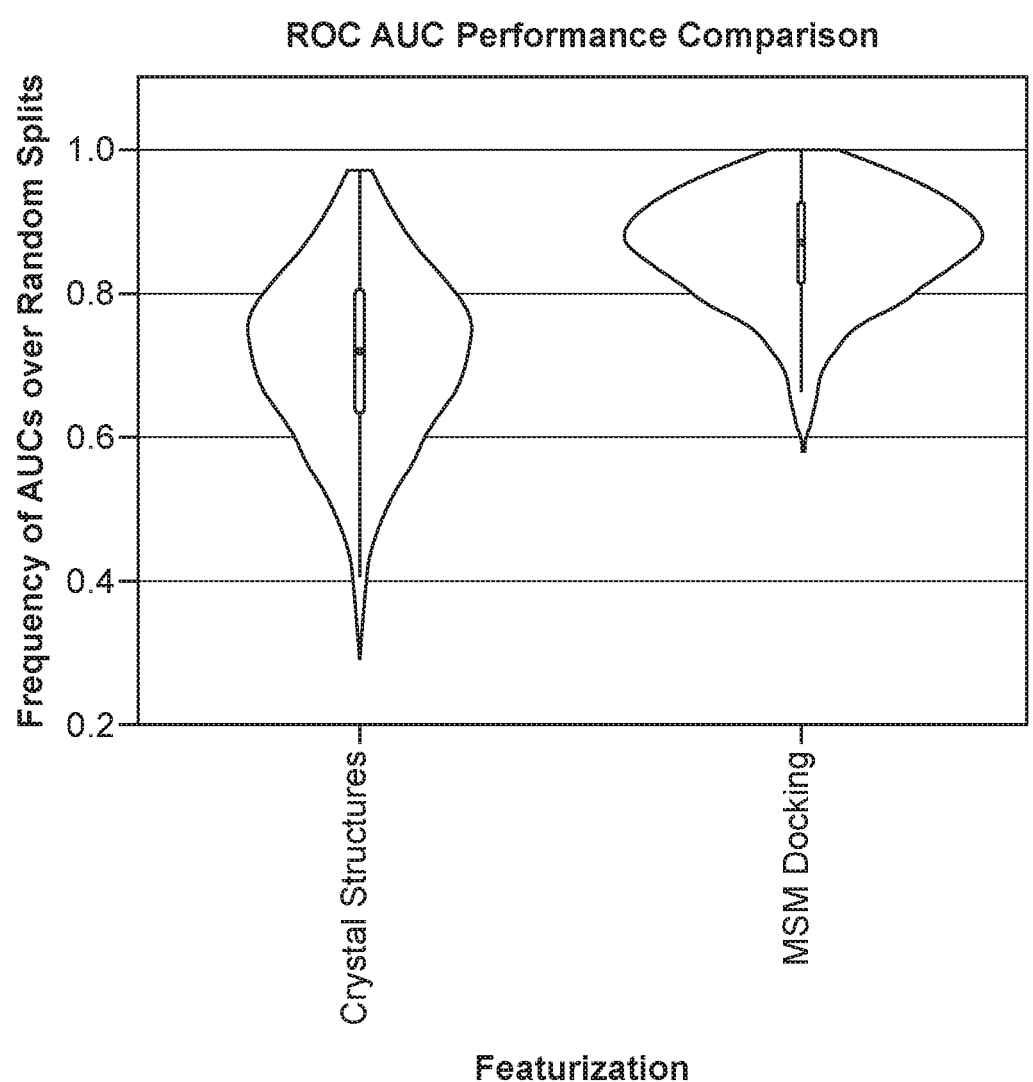
FIG. 4 shows violin plots comparing the two methods' (docking to crystal structures alone versus docking to crystal structures and MSM states) AUC performance over 1000 random train-test splits.

Modeling predicts that FMP4 binds to and facilitates activation of μOR in a unique way. In particular, FMP4 has a relatively high docking score for MD State 3, calculated to be important for agonism and binding. Note that tIC.1, the slowest tICA reaction coordinate, connects the two crystallographic states. In contrast, tIC.2, the second slowest coordinate, is kinetically orthogonal to tIC.1 and defines several non-crystallographic states (FIG. 1B). Measured by its progress along tIC.1 and by traditional metrics of GPCR literature[26,27] such as outward orientation of transmembrane helix 6 and bulged configuration of the NPxxY motif residues N332$^{7.48}$-Y336$^{7.53}$, MD State 3 is a novel active-like state of μOR. Near the orthosteric binding site, State 3 entails a rearrangement of Q124$^{2.60}$, M151$^{3.36}$, H297$^{6.52}$, Y299$^{6.54}$, and W318$^{6.35}$. The new positions of M151$^{3.36}$ and H297$^{6.52}$ enable FMP4 to occupy a pose that would be sterically forbidden in the active crystal structure (FIG. 1A). In contrast to the co-crystallized agonist, FMP4 engages in a π-T interaction with W293$^{6.48}$, a residue critical in gating μOR activation[10], and a hydrogen bond with H297$^{6.52}$. A PyMOL session and PDB files of each modeled μOR conformation is available, and further visualizations are shown in FIGS. 3A-3F.

Put together, by enumerating the state space of μOR, one can query conformations of the receptor to motivate rational design with all-atom structural information. An ineluctable flood of data stems from MD, and it is a significant data science challenge to derive actionable knowledge from a vast dataset of simulation alone. One millisecond of MD saved at one frame per nanosecond would contain one million conformations, far too many to be viewed by expert eyes. Rather, by pursuing a kinetically-motivated statistical approach, it was possible to discover key conformations of the receptor within a tractable scope.

The method described herein assists translational researchers in realizing a challenging goal: identifying novel GPCR drug scaffolds. Despite immense efforts in medicinal chemistry on synthesizing derivatives of existing chemotypes, all FDA-approved opioids are riddled with serious side effects that restrict their utility in treating acute and chronic pain. In this work, we describe a method to leverage crystallography and molecular modeling with machine learning to explore previously uncharted chemical space of molecules active at μOR. This approach is naturally applicable to any receptor which is expected to have any sort of conformational plasticity, including other GPCRs[31], kinases, ion channels, and nuclear receptors. The ultimate goal of superior opiate therapeutics remains in the future, but now may loom much closer on the horizon.

TABLE 1

Docking to both MD and crystal structures statistically significantly improves ability over crystal structures alone to distinguish μOR agonists from antagonists and μOR binders from non-binders. Table shows median ROC Area Under the Curve (AUC) performance over 1,000 train-validation splits. When either fentanyl or methadone analogs are removed from the training set (scaffold splits, cf. Methods), models remain able to distinguish fentanyl (or methadone) derivative agonists from antagonists. Similarly, when ligands with a Tanimoto similarity score greater than 0.7 to any other ligand in the database are removed from the training data (scaffold split), AUC improves commensurately when building a model incorporating MD-derived conformers. Therefore, models fit in this way have, in principle, the capacity to discover new opioid scaffolds in addition to derivatives of existing ones.

| Task | Split Type | AUC (Crystals alone) | AUC (Crystal + MD structures) |
|---|---|---|---|
| Agonism | Random | 0.73 | 0.85 |
| Agonism | Scaffold (Fentanyl) | 0.81 | 0.91 |
| Agonism | Scaffold (Methadone) | 0.89 | 0.94 |
| Binding | Random | 0.64 | 0.79 |
| Binding | Scaffold | 0.64 | 0.78 |

TABLE 2

Summary of MD simulations conducted of μOR.

| Simulation Ligand | Aggregate MD Simulation, Generation 1 | Aggregate MD Simulation, Generation 2 | Total Number of Trajectories |
|---|---|---|---|
| Apo | 115.839 μs | 119.620 μs | 512 |
| BU72 | 102.705 μs | 145.794 μs | 512 |
| Sufentanil | 105.298 μs | 166.723 μs | 754 |
| IBNtxA | 93.491 μs | 0 μs | 256 |
| TRV130 | 241.360 μs | 0 μs | 512 |
| | 1.090830 ms total | | 2,546 |

TABLE 3

List of agonists and antagonists used to fit machine learned classifiers. All ligands and labels derived from Wikipedia (en.wikipedia.org/wiki/Template:Opioidreceptormodulators), with some removed on advice by colleagues (cf. Acknowledgements section).

| name | action |
|---|---|
| 7-pet | agonist |
| acetylfentanyl | agonist |
| acetylmethadol | agonist |
| acrylfentanyl | agonist |
| ah-7921 | agonist |
| alfentanil | agonist |
| alimadol | agonist |
| 3-allylfentanyl | agonist |
| allylnorpethidine | agonist |
| allylprodine | agonist |
| alphacetylmethadol | agonist |
| alphamethadol | agonist |
| alphamethylthiofentanyl | agonist |
| anileridine | agonist |
| azaprocin | agonist |
| azidomorphine | agonist |
| bdpc | agonist |
| benzethidine | agonist |
| betacetylmethadol | agonist |
| betahydroxyfentanyl | agonist |
| betahydroxythiofentanyl | agonist |
| betamethadol | agonist |
| bezitramide | agonist |
| brifentanil | agonist |
| bromadoline | agonist |
| butyrfentanyl | agonist |
| c-8813 | agonist |
| carfentanil | agonist |
| cebranopadol | agonist |
| chloromorphide | agonist |
| chloroxymorphamine | agonist |
| ciprefadol | agonist |
| clonitazene | agonist |
| dadle | agonist |
| damgo | agonist |
| dermorphin | agonist |
| desmethylprodine | agonist |
| desomorphine | agonist |
| dextromoramide | agonist |
| dextropropoxyphene | agonist |
| diampromide | agonist |
| difenoxin | agonist |
| dihydroetorphine | agonist |
| dihydromorphine | agonist |
| dimenoxadol | agonist |
| dimepheptanol | agonist |
| dimethylaminopivalophenone | agonist |
| dioxaphetyl_butymte | agonist |
| diphenoxylate | agonist |
| dipipanone | agonist |
| dpi-3290 | agonist |
| eluxadoline | agonist |
| endomorphin | agonist |
| endomorphin-1 | agonist |
| endomorphin-2 | agonist |
| ethoheptazine | agonist |
| 14-ethoxymetopon | agonist |
| etonitazene | agonist |
| etorphine | agonist |
| etoxeridine | agonist |
| fentanyl | agonist |
| 4-fluorobutyrfentanyl | agonist |
| 4-fluoropethidine | agonist |
| furanylfentanyl | agonist |
| furethidine | agonist |
| hemorphin-4 | agonist |
| heterocodeine | agonist |
| hydromorphinol | agonist |
| hydromorphone | agonist |
| hydroxypethidine | agonist |
| ibntxa | agonist |

TABLE 3-continued

List of agonists and antagonists used to fit machine learned classifiers. All ligands and labels derived from Wikipedia (en.wikipedia.org/wiki/Template:Opioidreceptormodulators), with some removed on advice by colleagues (cf. Acknowledgements section).

| name | action |
| --- | --- |
| ic-26 | agonist |
| isomethadone | agonist |
| ketamine | agonist |
| ketobemidone | agonist |
| lefetamine | agonist |
| levacetylmethadol | agonist |
| levallorphan | agonist |
| levomethadone | agonist |
| levophenacylmorphan | agonist |
| levorphanol | agonist |
| lofentanil | agonist |
| loperamide | agonist |
| meprodine | agonist |
| metethoheptazine | agonist |
| methadone | agonist |
| metheptazine | agonist |
| 4-methoxybutyrfentanyl | agonist |
| 14-methoxydihydromorphinone | agonist |
| 14-methoxymetopon | agonist |
| alpha-methylacetylfentanyl | agonist |
| 3-methylbutyrfentanyl | agonist |
| n-methylcarfentanil | agonist |
| methyldesorphine | agonist |
| methyldihydromorphine | agonist |
| 6-methylenedihydrodesoxymorphine | agonist |
| 3-methylfentanyl | agonist |
| beta-methylfentanyl | agonist |
| methylketobemidone | agonist |
| 3-methylthiofentanyl | agonist |
| metopon | agonist |
| mitragynine_pseudoindoxyl | agonist |
| 6-monoacetylmorphine | agonist |
| morpheridine | agonist |
| morphine | agonist |
| morphine-6-glucuronide | agonist |
| morphinone | agonist |
| mr-2096 | agonist |
| mt-45 | agonist |
| nomcymethadol | agonist |
| ocfentanil | agonist |
| ohmefentanyl | agonist |
| oliceridine | agonist |
| oxpheneridine | agonist |
| oxymorphazone | agonist |
| oxymorphol | agonist |
| oxymorphone | agonist |
| parafluorofentanyl | agonist |
| pentamorphone | agonist |
| pepap | agonist |
| pethidine | agonist |
| phenadoxone | agonist |
| phenampromide | agonist |
| phenaridine | agonist |
| phenazocine | agonist |
| pheneridine | agonist |
| n-phenethylnordesomorphine | agonist |
| n-phenethylnormorphine | agonist |
| phenomorphan | agonist |
| phenoperidine | agonist |
| 4-phenylfentanyl | agonist |
| 14-phenylpropoxymetopon | agonist |
| picenadol | agonist |
| piminodine | agonist |
| piritramide | agonist |
| prodilidine | agonist |
| prodine | agonist |
| proheptazine | agonist |
| properidine | agonist |
| propylketobemidone | agonist |
| prosidol | agonist |
| pzm21 | agonist |
| r-4066 | agonist |
| r-30490 | agonist |
| racemorphan | agonist |
| remifentanil | agonist |
| ro4-1539 | agonist |
| sc-17599 | agonist |
| semorphone | agonist |
| sufentanil | agonist |
| thienorphine | agonist |
| thiofentanyl | agonist |
| tilidine | agonist |
| trefentanil | agonist |
| trimeperidine | agonist |
| trimu_5 | agonist |
| u-47700 | agonist |
| u-77891 | agonist |
| viminol | agonist |
| 6beta-naltrexol-d4 | antagonist |
| beta-chlornaltrexamine | antagonist |
| beta-funaltrexamine | antagonist |
| alvimopan | antagonist |
| at-076 | antagonist |
| axelopran | antagonist |
| bevenopran | antagonist |
| clocinnamox | antagonist |
| cyclofoxy | antagonist |
| cyprodime | antagonist |
| eptazocine | antagonist |
| ly-255582 | antagonist |
| methocinnamox | antagonist |
| methylnaltrexone | antagonist |
| methylsamidorphan | antagonist |
| nalmefene | antagonist |
| naloxazone | antagonist |
| naloxegol | antagonist |
| naloxol | antagonist |
| naloxonazine | antagonist |
| naloxone | antagonist |
| nattrexazone | antagonist |
| naltrexone | antagonist |
| oxilorphan | antagonist |
| quadazocine | antagonist |
| samidorphan | antagonist |

TABLE 4 a) A scaffold split was defined in which (1) agonist ligands with a Tanimoto score of ≤0.5 compared to fentanyl were placed in a train set, (2) agonist ligands with a Tanimoto score of ≥0.7 compared to fentanyl were placed in a test set, and (3) antagonists were randomly distributed between the train and test sets.

b) A scaffold split was defined in which (1) agonist ligands with a Tanimoto score of ≤0.5 compared to methadone were placed in a train set, (2) agonist ligands with a Tanimoto score of ≥0.7 compared to methadone were placed in a test set, and (3) antagonists were randomly distributed between the train and test sets.

TABLE 4-continued a)
Fentanyl analog ligands (test set):
['acetylfentanyl', 'acrylfentanyl', '3-allylfentanyl', 'alphamethylthiofentanyl',
'azaprocin', 'betahydroxyfentanyl', 'betahydroxythiofentanyl', 'butyrfentanyl',
'carfentanil', 'desmethylprodine', 'diampromide', 'fentanyl', '4-fluorobutyrfentanyl',
'furanylfentanyl', lofentanil', '4-methoxybutyrfentanyl', 'alpha-methylacetylfentanyl',
'3-methylbutyrfentanyl', 'n-methylcarfentanil', '3-methylfentanyl', 'beta-
methylfentanyl', '3-methylthiofentanyl', 'ocfentanil', 'ohmefentanyl',
'parafluorofentanyl', 'pepap', 'phenampromide', 'phenaridine', '4-phenylfentanyl',
'prodilidine', 'prodine', 'proheptazine', 'prosidol', 'r-30490', 'remifentanil', 'sufentanil',
'thiofentanyl', 'trimeperidine', 'u-47700']
Non-fentanyl-analog agonists (train set):
['7-pet', 'alimadol', 'alphamethadol', 'azidomorphine', 'bdpc', 'betamethadol', 'c-8813',
'cebranopadol', 'chloromorphide', 'chloroxymorphamine', 'ciprefadol', 'clonitazene',
'dadle', 'damgo', 'desomorphine', 'dihydroetorphine', 'dihydromorphine', 'dimenoxadol',
'dimepheptanol', 'dimethylaminopivalophenone', 'eluxadoline', 'endomorphin',
'endomorphin-1', '14-ethoxymetopon', 'etonitazene', 'etorphine', 'hemorphin-4',
'heterocodeine', 'hydromorphinol', 'hydromorphone', 'ibntxa', 'ketamine', 'lefetamine',
'levophenacylmorphan', 'levorphanol', '14-methoxydihydromorphinone', '14-
methoxymetopon', 'methyldesorphine', 'methyldihydromorphine', '6-
methylenedihydrodesoxymorphine', 'metopon', 'mitragynine_pseudoindoxyl', '6-
monoacetylmorphine', 'morphine', 'morphine-6-glucuronide', 'morphinone', 'mr-2096',
'oliceridine', 'oxymorphazone', 'oxymorphol', 'oxymorphone', 'pentamorphone',
'phenazocine', 'n-phenethylnordesomorphine', 'n-phenethylnormorphine',
'phenomorphan', '14-phenylpropoxymetopon', 'picenadol', 'pzm21', 'racemorphan',
'ro4-1539', 'sc-17599', 'semorphone', 'thienorphine', 'tilidine', 'trimu_5', 'viminol']
Antagonists:
['levallorphan', '6beta-naltrexol-d4', 'beta-chlornaltrexamine', 'beta-funaltrexamine',
'alvimopan',
'at-076', 'axelopran', 'bevenopran', 'clocinnamox', 'cyclofoxy', 'cyprodime',
'eptazocine', 'ly-255582', 'methocinnamox', 'methylnaltrexone', 'methylsamidorphan',
'nalmefene', 'naloxazone', 'naloxegol', 'naloxol', 'naloxonazine', 'naloxone',
'naltrexazone', 'naltrexone', 'oxilorphan', 'quadazocine', 'samidorphan']
b)
Methadone analog ligands (test set).
['acetylmethadol', 'alphacetylmethadol', 'alphamethadol', 'betacetylmethadol',
'betamethadol', 'dipipanone', 'ic-26', 'isomethadone', 'ketobemidone',
'levacetylmethadol', 'levomethadone', 'methadone', 'methylketobemidone',
'noracymethadol', 'phenadoxone', 'propylketobemidone', 'r4066']
Non-methadone analogs (train set).
['7-pet', 'alimadol', 'azidomorphine', 'bdpc', 'c-8813', 'cebranopadol', 'chloromorphide',
'chloroxymorphamine', 'ciprefadol', 'clonitazene', 'dadle', 'damgo', 'desomorphine',
'dihydroetorphine', 'dihydromorphine', 'dimenoxadol', 'dimepheptanol',
'dimethylaminopivalophenone', 'eluxadoline', 'endomorphin', 'endomorphin-1', '14-
ethoxymetopon', 'etonitazene', 'etorphine', 'hemorphin-4', 'heterocodeine',
'hydromorphinol', 'hydromorphone', 'ibntxa', 'ketamine', 'lefetamine',
'levophenacylmorphan', 'levorphanol', '14-methoxydihydromorphinone', '14-
methoxymetopon', 'methyldesorphine', 'methyldihydromorphine', '6-
methylenedihydrodesoxymorphine', 'metopon', 'mitragynine_pseudoindoxyl', '6-
monoacetylmorphine', 'morphine', 'morphine-6-glucuronide', 'morphinone', 'mr-2096',
'oliceridine', 'oxymorphazone', 'oxymorphol', 'oxymorphone', 'pentamorphone',
'phenazocine', 'n-phenethylnordesomorphine', 'n-phenethylnormorphine',
'phenomorphan', '14-phenylpropoxymetopon', 'picenadol', 'pzm21', 'racemorphan',
'ro4-1539', 'sc-17599', 'semorphone', 'thienorphine', 'tilidine', 'trimu_5', 'viminol']
Antagonists:
['levallorphan', '6beta-naltrexol-d4', 'beta-chlornaltrexamine', 'beta-funaltrexamine',
'alvimopan', 'at-076', 'axelopran', 'bevenopran', 'clocinnamox', 'cyclofoxy', 'cyprodime',
'eptazocine', 'ly-255582', 'methocinnamox', 'methylnaltrexone', 'methyl samidorphan',
'nalmefene', 'naloxazone', 'naloxegol', 'naloxol', 'naloxonazine', 'naloxone',
'naltrexazone', 'naltrexone', 'oxilorphan', 'quadazocine', 'samidorphan']

TABLE 5

Random Forest average Gini impurity reduction ("importance") of each feature (MD State, Crystal Structure) for a) distinguishing between opioid agonists and antagonists and b) distinguishing between binders and non-binders from μOR.

| | | | |
|---|---|---|---|
| a) | | | |
| Inactive | Crystal | | |
| State | 14 | 0.033463 | |
| State | 3 | 0.031175 | |
| State | 17 | 0.029950 | |
| State | 10 | 0.029853 | |
| State | 23 | 0.025154 | |
| State | 5 | 0.024361 | |

TABLE 5-continued

Random Forest average Gini impurity reduction ("importance") of each feature (MD State, Crystal Structure) for a) distinguishing between opioid agonists and antagonists and b) distinguishing between binders and non-binders from μOR.

| | | |
|---|---|---|
| State | 16 | 0.023912 |
| State | 21 | 0.023884 |
| State | 4 | 0.021384 |
| State | 22 | 0.020618 |
| State | 0 | 0.019934 |
| State | 13 | 0.019720 |
| State | 18 | 0.017975 |
| State | 7 | 0.017955 |
| State | 24 | 0.017434 |
| State | 11 | 0.017295 |
| State | 9 | 0.016170 |
| State | 8 | 0.015486 |
| State | 15 | 0.015193 |
| State | 19 | 0.013673 |
| Active | Crystal | 0.013580 |
| State | 12 | 0.013346 |
| State | 6 | 0.012534 |
| State | 2 | 0.012306 |
| State | 1 | 0.012289 |
| State | 20 | 0.011230 |
| b) | | |
| Inactive | Crystal | 0.057546 |
| State | 18 | 0.051126 |
| State | 2 | 0.050497 |
| State | 14 | 0.045177 |

TABLE 5-continued

Random Forest average Gini impurity reduction ("importance") of each feature (MD State, Crystal Structure) for a) distinguishing between opioid agonists and antagonists and b) distinguishing between binders and non-binders from μOR.

| | | |
|---|---|---|
| State | 1 | 0.043236 |
| Active | Crystal | 0.040393 |
| State | 20 | 0.039999 |
| State | 3 | 0.037063 |
| State | 24 | 0.035946 |
| State | 19 | 0.035883 |
| State | 17 | 0.035723 |
| State | 5 | 0.035547 |
| State | 22 | 0.034922 |
| State | 16 | 0.034121 |
| State | 0 | 0.034035 |
| State | 21 | 0.033999 |
| State | 4 | 0.033884 |
| State | 6 | 0.033837 |
| State | 13 | 0.033381 |
| State | 10 | 0.032723 |
| State | 11 | 0.032537 |
| State | 23 | 0.032248 |
| State | 12 | 0.032069 |
| State | 9 | 0.031896 |
| State | 15 | 0.031409 |
| State | 8 | 0.030558 |
| State | 7 | 0.030245 |

TABLE 6

Docking to both MD states and crystal structures statistically significantly improves ability over crystals alone to distinguish μOR binders from non-binders. Table shows median ROC Area Under the Curve (AUC) performance over the validation set over 1,000 train-valid splits for different split and model types. Differences between crystal lone and crystal + MD structures methods are considered statistically significant if the lower bound of a 99% Wilson scoring confidence interval (CI) is greater than 0.5.

| Dataset | Cross validation split type | AUC (Crystals alone) | AUC (Crystal + MD structures) | Wilson 99% CI |
|---|---|---|---|---|
| Wikipedia Agonists/Antagonists | Random | 0.72 | 0.86 | (0.82, 0.88) |
| Wikipedia Agonists/Antagonists | Methadone | 0.84 | 0.99 | (0.82, 0.88) |
| Wikipedia Agonists/Antagonists | Fentanyl | 0.77 | 0.93 | (0.98, 1.0) |
| Expert curated dataset | Random | 0.73 | 0.85 | (0.67, 0.75) |
| Expert curated dataset | Methadone | 0.89 | 0.94 | (0.51, 0.59) |
| Expert curated dataset | Fentanyl | 0.81 | 0.91 | (0.88, 0.93) |

Note that, for each dataset, incorporating MD-derived structures in addition to the crystal structures confers a statistically significant improvement in ability to distinguish binders from non-binder as measured by AUC. Notably, when fentanyl (or methadone) analogs are removed from the training set, models remain able to distinguish fentanyl (or methadone) derivative agonists from random sets of antagonists. This indicates that models fit in this way have the capacity to discover new opioid agonist scaffolds in addition to derivatives of existing ones.

TABLE 7

Docking to both MD states and crystal structures statistically significantly improves ability over crystals alone to distinguish μOR binders from non-binders. Table shows median ROC Area Under the Curve (AUC) performance over the validation set over 1,000 train-valid splits for different split and model types. Differences between crystal lone and crystal + MD structures methods are considered statistically significant if the lower bound of a 99% Wilson scoring confidence interval (CI) is greater than 0.5.

| Dataset | Split | AUC (Crystals alone) | AUC (Crystal + MD structures) | Wilson 99% CI |
|---|---|---|---|---|
| Measured pIC50, cutoff = 6.0 | Random | 0.59 | 0.64 | (0.76, 0.82) |
| Measured pIC50, cutoff = 7.0 | Random | 0.59 | 0.71 | (0.99, 1.0) |
| Measured pIC50 cutoff = 8.0 | Random | 0.58 | 0.74 | (0.99, 1.0) |
| All, pIC50 cutoff = 5.3 | Random | 0.78 | 0.87 | (0.99, 1.0) |
| All, pIC50 cutoff = 6.0 | Random | 0.73 | 0.82 | (0.99, 1.0) |
| All, pIC50 cutoff = 7.0 | Random | 0.67 | 0.78 | (0.99, 1.0) |
| All, pIC50 cutoff = 8.0 | Random | 0.65 | 0.79 | (0.99, 1.0) |
| All, pIC50 cutoff = 5.3 | Scaffold | 0.77 | 0.81 | (0.73, 0.80) |
| All, pIC50 cutoff = 6.0 | Scaffold | 0.78 | 0.83 | (0.73, 0.8) |
| All, pIC50 cutoff = 7.0 | Scaffold | 0.66 | 0.79 | (0.86, 0.91) |
| All, pIC50 cutoff = 8.0 | Scaffold | 0.64 | 0.78 | (0.85, 0.9) |

Note that, for each dataset, incorporating MD-derived structures in addition to the crystal structures confers a statistically significant improvement in ability to distinguish binders from non-binder as measured by AUC. Notably, when molecules with similar scaffolds (as measured by a Tanimoto similarity score of >0.7) are removed from the training data, models remain able to distinguish binders from non-binders. This indicates that models fit in this way have the capacity to discover new opioid scaffolds in addition to derivatives of existing ones. Datasets consist of compounds with experimentally known values of binding affinity to μOR according to Chembl, Wikipedia, and other publicly available sources (full list of ligands in this dataset available in supplemental files). Datasets termed "Measured Ki" include only those compounds with a real-numbered Ki value listed in Chembl; datasets termed "All" also include compounds that have no listed Ki but are termed "Not Active" by Chembl. Therefore, "Measured Ki" datasets are subsets of the "All" series of datasets. Binders are considered to be compounds with a pIC50 greater than some cutoff (listed in the "Dataset" table) and non-binders with a pIC50 lower than that same cutoff. For example, "All, pIC50 cutoff = 7.0" indicates a dataset wherein (a) both ligands with a measurable pIC50 <7.0 and those listed as "Not Active" in Chembl are considered non-binders, and (b) both ligands with a measurable pIC50 ≥ 7.0 and other known agonists and antagonists from Wikipedia are considered to be binders.

TABLE 8

List of all 32 purchased compounds that were experimentally tested for binding.

| FMP # | Supplier | Catalogue no. | Molecular Weight | Structure |
|---|---|---|---|---|
| 1 | ChemBridge Corp | 5315117 | 261.409 | 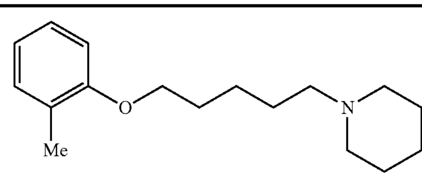 |
| 2 | Vitas-M Laboratory | STK246443 | 220.272 | 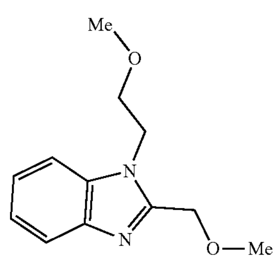 [SMILES: COCCn1c(COC)nc2ccccc21] |
| 3 | ChemBridge Corp | 5421855 | 298.471 | 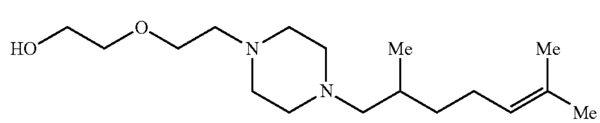 [SMILES: CC(C)=CCCC(C)CN1CCN(CCOCCO)CC1] |
| 4 | ChemBridge Corp | 5359784 | 286.419 | 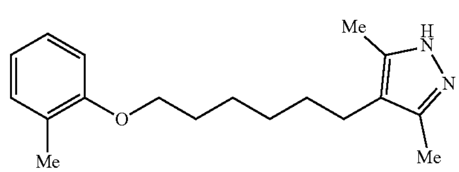 [SMILES: Cc1ccccc1OCCCCCCc1c(C)n[nH]c1C] |

TABLE 8-continued
List of all 32 purchased compounds that were experimentally tested for binding.
| FMP # | Supplier | Catalogue no. | Molecular Weight | Structure |
|---|---|---|---|---|
| 5 | ChemDiv, Inc. | K416-0034 | 331.45 | 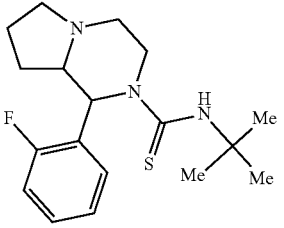 [SMILES: CC(C)(C)NC(=S)N1CCN2CCCC2C1c1ccccc1F] |
| 6 | ChemDiv, Inc. | 6030-4029 | 277.408 | 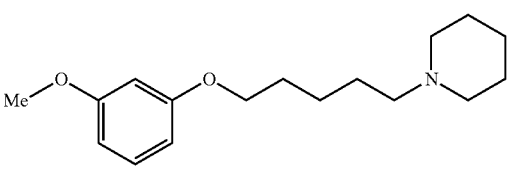 [SMILES: COc1cccc(OCCCCCN2CCCCC2)c1] |
| 7 | ChemDiv, Inc. | D171-0103 | 284.403 | 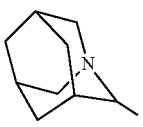 |
| 8 | ChemDiv, Inc. | K808-9296 | 317.388 | 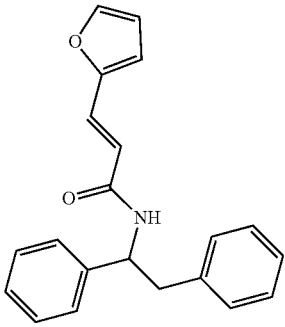 [SMILES: O=C(/C=C/c1ccco1)NC(Cc1ccccc1)c1ccccc1] |
| 9 | ChemDiv, Inc. | C296-0706 | 379.43 | 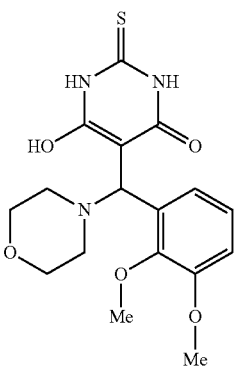 [SMILES: COc1cccc(C(c2c(O)[nH]c(=S)[nH]c2=O)N2CCOCC2)c1OC] |

TABLE 8-continued

List of all 32 purchased compounds that were experimentally tested for binding.

| FMP # | Supplier | Catalogue no. | Molecular Weight | Structure |
|---|---|---|---|---|
| 10 | ChemDiv, Inc. | C656-0381 | 347.353 | 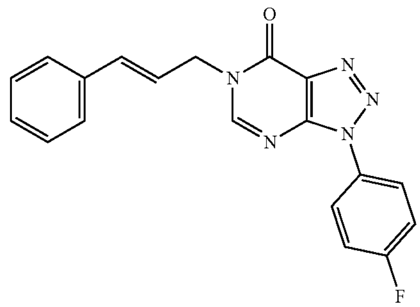 [SMILES: O=c1c2nnn(-c3ccc(F)cc3)c2ncn1C/C=C/c1ccccc1] |
| 11 | InterBioScreen Ltd. | STOCK1S-36272 | 255.4 | 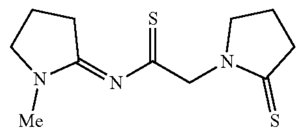 [SMILES: CN1CCC/C1=N\C(=S)CN1CCCC1=S] |
| 12 | Life Chemicals Inc. | F5959-0041 | 249.33 | 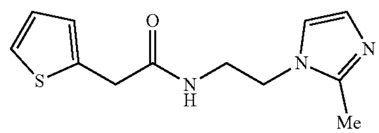 [SMILES: Cc1nccn1CCNC(=O)Cc1cccs1] |
| 13 | Life Chemicals Inc. | F6350-0021 | 228.31 | 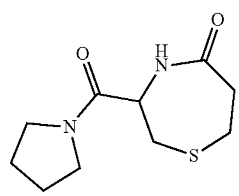 [SMILES: O=C1CCSCC(C(=O)N2CCCC2)N1] |
| 14 | MayBridge, Ltd. | S14427 | 325.324 | 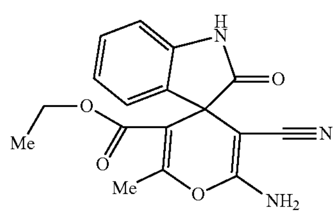 [SMILES: CCOC(=O)C1=C(C)OC(N)=C(C#N)C12C(=O)Nc1ccccc12] |
| 15 | MayBridge, Ltd. | CC52213 | 207.273 | 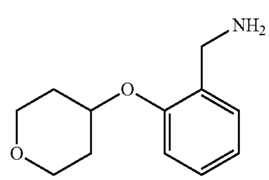 [SMILES: NCc1ccccc1OC1CCOCC1] |
| 16 | Specs | AG-644/14117620 | 286.419 | 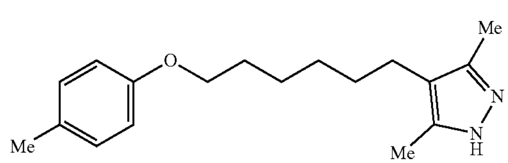 [SMILES: Cc1ccc(OCCCCCCc2c(C)n[nH]c2C)cc1] |
| 17 | Specs | AF-399/41900457 | 282.77 | 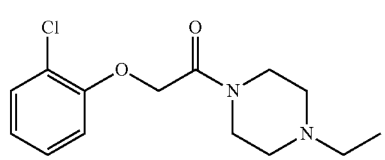 [SMILES: CCN1CCN(C(=O)COc2ccccc2Cl)CC1] |

TABLE 8-continued

List of all 32 purchased compounds that were experimentally tested for binding.

| FMP # | Supplier | Catalogue no. | Molecular Weight | Structure |
|---|---|---|---|---|
| 18 | Specs | AK-968/13031275 | 335.23 | 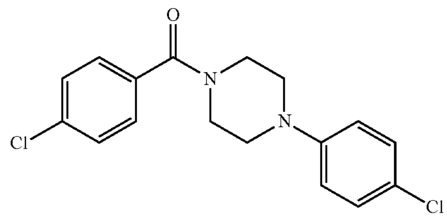 [SMILES: O=C(c1ccc(Cl)cc1)N1CCN(c2ccc(Cl)cc2)CC1] |
| 19 | Specs | AG-690/11549877 | 265.353 | 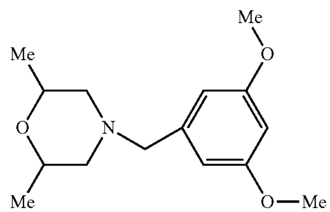 [SMILES: COc1cc(CN2CC(C)OC(C)C2)cc(OC)c1] |
| 20 | Specs | AF-399/41875794 | 291.435 | 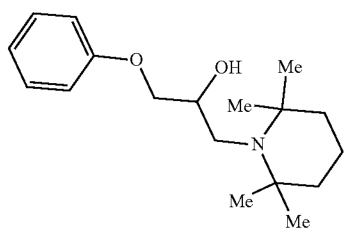 [SMILES: CC1(C)CCCC(C)(C)N1CC(O)COc1ccccc1] |
| 21 | Specs | AG-664/15584112 | 290.451 | 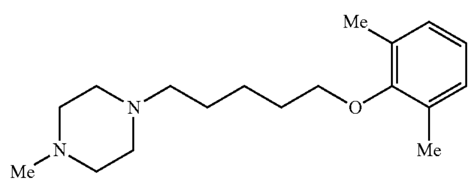 [SMILES: Cc1cccc(C)c1OCCCCCN1CCN(C)CC1] |
| 22 | Specs | AG-690/11764068 | 308.422 | 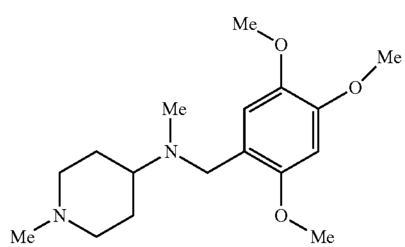 [SMILES: COc1cc(OC)c(OC)cc1CN(C)C1CCN(C)CC1] |
| 23 | Vitas-M Laboratory | STK768975 | 354.47 | 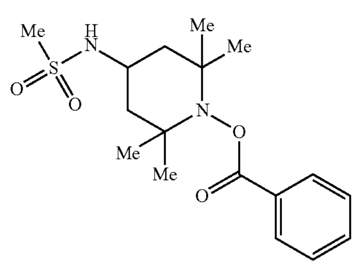 [SMILES: CC1(C)CC(NS(C)(=O)=O)CC(C)(C)N1OC(=O)c1ccccc1] |

TABLE 8-continued

List of all 32 purchased compounds that were experimentally tested for binding.

| FMP # | Supplier | Catalogue no. | Molecular Weight | Structure |
|---|---|---|---|---|
| 24 | Vitas-M Laboratory | STK825555 | 408.28 | 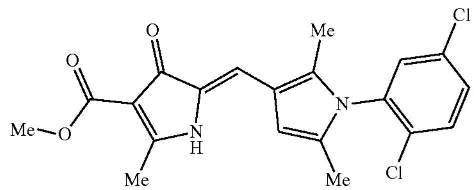 [SMILES: COC(=O)C1=C(C)N/C(=C\c2cc(C)n(-c3cc(Cl)ccc3Cl)c2C)C1=O] |
| 25 | Vitas-M Laboratory | STK705512 | 390.399 | 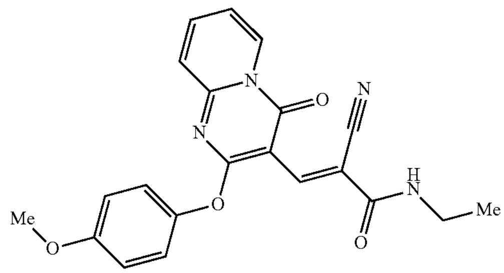 [SMILES: CCNC(=O)/C(C#N)=C/c1c(Oc2ccc(OC)cc2)nc2ccccn2c1=O] |
| 26 | Vitas-M Laboratory | STL181788 | 309.453 | 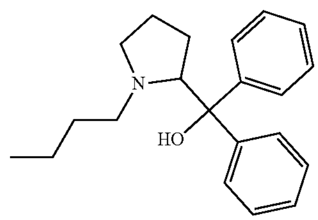 [SMILES: CCCCN1CCCC1C(O)(c1ccccc1)c1ccccc1] |
| 27 | Vitas-M Laboratory | STK123054 | 253.301 | 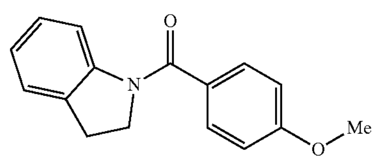 [SMILES: COc1ccc(C(=O)N2CCc3ccccc32)cc1] |
| 28 | Vitas-M Laboratory | STK386756 | 343.28 | 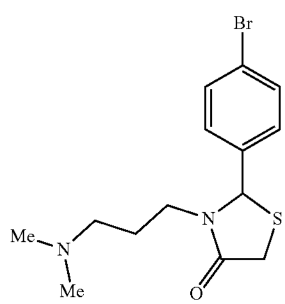 [SMILES: CN(C)CCCN1C(=O)CSC1c1ccc(Br)cc1] |
| 29 | Vitas-M Laboratory | STK766152 | 285.387 | 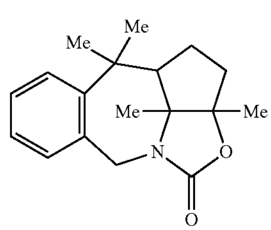 |

TABLE 8-continued

List of all 32 purchased compounds that were experimentally tested for binding.

| FMP # | Supplier | Catalogue no. | Molecular Weight | Structure |
|---|---|---|---|---|
| 30 | ChemBridge Corp | 5316199 | 263.381 | 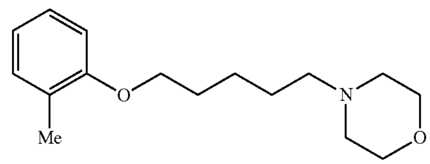 [SMILES: Cc1ccccc1OCCCCCN1CCOCC1] |
| 31 | ChemBridge Corp | 5455149 | 225 | 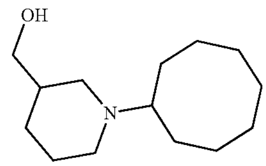 [SMILES: OCC1CCCN(C2CCCCCCC2)C1] |
| 32 | ChemBridge Corp | 5410648 | 280 | 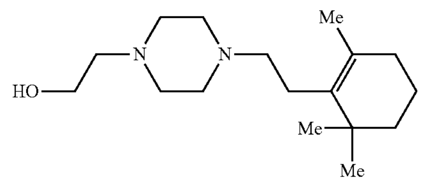 [SMILES: CC1=C(CCN2CCN(CCO)CC2)C(C)(C)CCC1] |

TABLE 9

Receptor binding of FMP4 and structurally similar analogs

| | | | Binding Data-Ki(nM)[a] | | |
|---|---|---|---|---|---|
| FMP# | Structure | MW | MOR-1 | KOR-1 | DOR-1 |
| 1 | | 261.409 | 841.4 ± 241.9 | 7386 ± 2376 | 17874 ± 7615 |
| 4 | | 286.419 | 3217 ± 153 | 2503 ± 523 | 8143 ± 1398 |
| 6 | | 277.408 | >30 μM | 6941 ± 1970 | >30 μM |
| 16 | | 286.419 | 1748 ± 492 | 4918 ± 2235 | 9058 ± 566 |

TABLE 9-continued

Receptor binding of FMP4 and structurally similar analogs

| FMP# | Structure | MW | Binding Data-Ki(nM)[a] | | |
|---|---|---|---|---|---|
| | | | MOR-1 | KOR-1 | DOR-1 |
| 21 | | 290.451 | >30 μM | 5503 ± 4194 | >30 μM |
| 30 | | 263.381 | 11315 ± 2262 | 6009 ± 2163 | 12761 ± 856 |
| DAMGO | | | 3.3 ± 0.43[b] | | |
| U50, 488h | | | | 0.73 ± 0.32[b] | |
| DPDPE | | | | | 1.39 ± 0.67[b] |

[a]Competition studies were performed with the indicated compounds against $^{125}$I-IBNtxA (0.1 nM) in membranes from CHO cells stably expressing the indicated cloned mouse opioid receptors. Results are presented as nM ± SEM from three independent experiments performed in triplicate.
[b]Values from the literature.[8]

REFERENCES

1. Overington, J. P., Al-Lazikani, B. & Hopkins, A. L. *Nat. Rev. Drug Discov.* 5, 993-996 (2006).
2. Pasternak, G. W. & Pan, Y.-X. *Pharmacol. Rev.* 65, 1257-1317 (2013).
3. Staus, D. P. et al. *Nature* 535, 448-452 (2016).
4. Manglik, A. et al. *Cell* 161, 1101-1111 (2015).
5. Manglik, A. et al. *Nature* 1-6 (2016).
6. Okude, J. et al. *Angew. Chemie* 127, 15997-16002 (2015).
7. Majumdar, S. et al. *Proc. Natl. Acad. Sci.* 108, 19778-19783 (2011).
8. Váradi, A. et al. *J. Med. Chem.* (2016).
9. Sounier, R. et al. *Nature* 524, 375-378 (2015).
10. Huang, W. et al. *Nature* 524, 315-21 (2015).
11. Manglik, A. et al. *Nature* 485, 321-326 (2012).
12. Neilan, C. L. et al. *Eur. J. Pharmacol.* 499, 107-116 (2004).
13. Niemegeers, C. J., Schellekens, K. H., Van Bever, W. F. & Janssen, P. A. *Arzneimittelforschung.* 26, 1551-1556 (1975).
14. Chen, X.-T. et al. *J. Med. Chem.* 56, 8019-8031 (2013).
15. Feinberg, E. N., Farimani, A. B., Hernandez, C. X. & Pande, V. S. *bioRxiv* 170886 (2017).
16. Huang, W. et al. *Nature* 524, 315-21 (2015).
17. Schwantes, C. R. & Pande, V. S. *J. Chem. Theory Comput.* 9, 2000-2009 (2013).
18. Pérez-Hernández, G., Paul, F., Giorgino, T., De Fabritiis, G. & Noé, F. *J. Chem. Phys.* 139, 15102 (2013).
19. McGibbon, R. T., Husic, B. E. & Pande, V. S. *J. Chem. Phys.* 146, 44109 (2017).
20. Sculley, D. *Proc. 19th Int. Conf. World wide web* 1177-1178 (2010).
21. Offutt, T. L., Swift, R. V & Amaro, R. E. *J. Chem. Inf. Model.* (2016).
22. Weiss, D. R. et al.*ACS Chem. Biol.* 8, 1018-1026 (2013).
23. Breiman, L. *Mach. Learn.* 45, 5-32 (2001).
24. Friedman, J., Hastie, T. & Tibshirani, R.1, (Springer series in statistics Springer, Berlin: 2001).
25. Goldberg, J. S. *Perspect. Medicin. Chem.* 4, 1 (2010).
26. Dror, R. O. et al. *Proc. Natl. Acad. Sci.* 108, 18684-18689 (2011).
27. Latorraca, N. R., Venkatakrishnan, A. J. & Dror, R. O. *Chem. Rev.* (2016).
28. Sherman, W., Beard, H. S. & Farid, R. *Chem. Biol. Drug Des.* 67, 83-84 (2006).
29. Clark, A. J. et al. *J. Chem. Theory Comput.* 12, 2990-2998 (2016).
30. Nabuurs, S. B., Wagener, M. & De Vlieg, J. *J. Med. Chem.* 50, 6507-6518 (2007).
31. Feinberg, E. N. & Pande, V. S. *Prep* (2016).

While the preferred embodiments of the invention have been illustrated and described, it will be appreciated that various changes can be made therein without departing from the spirit and scope of the invention.

What is claimed is:

1. A method of activating an opioid receptor, the method comprising contacting the opioid receptor with an effective amount of a composition comprising 3,5-dimethyl-4-[6-(o-tolyloxy)hexyl]-1H-pyrazole (FMP4), 1-piperidino-5-(o-tolyloxy)pentane (FMP1), or 3,5-dimethyl-4-[6-(p-tolyloxy) hexyl]-1H-pyrazole (FMP16), or a pharmaceutically acceptable salt thereof, or a combination thereof.

2. The method of claim 1, wherein the opioid receptor is selected from the group consisting of a μ-opioid receptor (MOR), a δ-opioid receptor (DOR), and a κ-opioid receptor (KOR).

3. The method of claim 1, wherein the composition further comprises a pharmaceutically acceptable excipient.

4. A method of treating pain, diarrhea, or a drug overdose in a subject, the method comprising administering a therapeutically effective amount of a composition comprising 3,5-dimethyl-4-[6-(o-tolyloxy)hexyl]-1H-pyrazole (FMP4), 1-piperidino-5-(o-tolyloxy)pentane (FMP 1), 3,5-dimethyl-4-[6-(p-tolyloxy)hexyl]-1H-pyrazole (FMP16), or a pharmaceutically acceptable salt thereof, or a combination thereof to the subject.

5. The method of claim 4, wherein the composition further comprises a pharmaceutically acceptable excipient.

6. The method of claim 4 or 5, wherein multiple cycles of treatment are administered to the subject.

7. The method of claim 6, wherein the compound is administered intermittently.

8. The method of claim 6, wherein the composition is administered according to a daily dosing regimen.

9. The method of claim 4, wherein the composition is administered orally, intravenously, or subcutaneously.

10. The method of claim 4, wherein the pain is post-operative pain, traumatic pain, neuropathic pain, or inflammatory pain.

11. The method of claim 4, wherein the subject is human.

* * * * *